United States Patent
Craven et al.

(10) Patent No.: US 10,952,441 B2
(45) Date of Patent: Mar. 23, 2021

(54) SYMBIONT FOR ENHANCEMENT OF PLANT PERFORMANCE

(71) Applicant: Noble Research Institute, LLC, Ardmore, OK (US)

(72) Inventors: Kelly Craven, Ardmore, OK (US); Prasun Ray, Ardmore, OK (US)

(73) Assignee: NOBLE RESEARCH INSTITUTE, LLC, Ardmore, OK (US)

(*) Notice: Subject to any disclaimer, the term of this patent is extended or adjusted under 35 U.S.C. 154(b) by 282 days.

(21) Appl. No.: 15/626,926

(22) Filed: Jun. 19, 2017

(65) Prior Publication Data

US 2017/0360049 A1 Dec. 21, 2017

Related U.S. Application Data

(63) Continuation of application No. PCT/US2017/035844, filed on Jun. 2, 2017.

(60) Provisional application No. 62/345,766, filed on Jun. 4, 2016.

(51) Int. Cl.
*A01N 63/04* (2006.01)
*A01N 25/00* (2006.01)
*A01N 25/08* (2006.01)
*A01N 63/30* (2020.01)

(52) U.S. Cl.
CPC .............. *A01N 63/30* (2020.01); *A01N 25/00* (2013.01)

(58) Field of Classification Search
None
See application file for complete search history.

(56) References Cited

U.S. PATENT DOCUMENTS

| 8,975,489 B2 | 3/2015 | Craven | |
|---|---|---|---|
| 2002/0115084 A1 | 8/2002 | Barnett et al. | |
| 2007/0016974 A1 | 1/2007 | Byrum et al. | |
| 2010/0024076 A1* | 1/2010 | Craven | A01H 3/00 800/301 |
| 2012/0021906 A1* | 1/2012 | Sutton | A01N 63/04 504/117 |
| 2012/0198590 A1 | 8/2012 | Miller et al. | |
| 2015/0073048 A1 | 3/2015 | Gandhi et al. | |
| 2015/0335029 A1 | 11/2015 | Mitter et al. | |

OTHER PUBLICATIONS

Ghimire et al., BioEnergy Research, vol. 2, No. 1-2, pp. 51-58 (2009).*
Weiss et al. Sebacinales—One Thousand and One Interactions With Land Plants' New Phytologist, Feb. 5, 2016, vol. 211, No. 1, pp. 20-40; summary; figure 3 legend; p. 35, first column, third paragraph.
International Search Report dated Oct. 20, 2017 for International Patent Application No. PCT/US17/35844.
Extended European Search Report dated Feb. 6, 2020 for EP Application No. 17807634.5.
Ray Prasun et al: "Sebacinavermifera: a unique root symbiont with vast agronomic potential", World Journal of Microbiology and Biotechnology; vol. 32, No. 1, Dec. 29, 2015, pp. 1-10.
Sitar. Ghimire et al: "The Mycorrhizal Fungus, Sebacina vermifera, Enhances Seed Germination and Biomass Production in Switchgrass (*Panicum virgatum* L)", Bioenergy Research, vol. 2, No. 1-2, Apr. 16, 2009, pp. 51-58.
Sitar. Ghimire et al: "Enhancement of Switchgrass (*Panicum virgatum* L.) Biomass Production under Drought Conditions by the Ectomycorrhizal Fungus *Sebacina vermifera*", Applied and Environmental Microbiology, vol. 77, No. 19, Aug. 12, 2011, pp. 7063-7067.
Ray Prasun et al: "A Novel Delivery System for the Root Symbiotic Fungus,*Sebacina vermifera*, and Consequent Biomass Enhancement of Low Lignin COMT Switchgrass Lines", Bioenergy Research, vol. 8, No. 3, Jun. 12, 2015, pp. 922-933.
Franz Oberwinkler et al: "Enigmatic Sebacinales", Mycological Progress, vol. 12, No. 1, Jan. 4, 2013, pp. 1-27.

* cited by examiner

*Primary Examiner* — Soren Harward
*Assistant Examiner* — Paul D. Pyla
(74) *Attorney, Agent, or Firm* — Barnes & Thornburg LLP; Ryan P. Cox

(57) ABSTRACT

The present disclosure provides a novel endophyte, *Serendipita vermifera* ssp. *bescii* ("*S. bescii*"), uses thereof and methods incorporating the use thereof for enhancement of plant performance. The present disclosure also provides methods for detecting the presence of and identifying *S. bescii*.

10 Claims, 38 Drawing Sheets
(33 of 38 Drawing Sheet(s) Filed in Color)
Specification includes a Sequence Listing.

Fig. 4

```
                       1         10        20        30        40        50        60
                       |          |         |         |         |         |         |
      Sbescii    GGTTCGATTAGTCTTTCGCCCCTATACCCAAATTTGACGATCGATTTGCACGTCAGAATC
   C2-TC-Orchid  GGTTCGATTAGTCTTTCGCCCCTATACCCAAATTTGACGATCGATTTGCACGTCAGAATC
         C2-TC  GGTTCGATTAGTCTTTCGCCCCTATACCCAAATTTGACGATCGATTTGCACGTCAGAATC
       C2-NFSgF  GGTTCGATTAGTCTTTCGCCCCTATACCCAAATTTGACGATCGATTTGCACGTCAGAATC Sbescii    GCTACGAGCCTCCACCAGAGTTTCCTCTGGCTTCACCCTATTCAGGCATAGTTCACCATC
   C2-TC-Orchid  GCTACGAGCCTCCACCAGAGTTTCCTCTGGCTTCACCCTATTCAGGCATAGTTCACCATC
         C2-TC  GCTACGAGCCTCCACCAGAGTTTCCTCTGGCTTCACCCTATTCAGGCATAGTTCACCATC
       C2-NFSgF  GCTACGAGCCTCCACCAGAGTTTCCTCTGGCTTCACCCTATTCAGGCATAGTTCACCATC Sbescii    TTTCGGGTCCCAACATATGCGCTCTGCCGCAGATGCGTCACAGAAGGTCTGCTCCGGGCG
   C2-TC-Orchid  TTTCGGGTCCCAACATATGCGCTCTGCCGCAGATGCGTCACAGAAGGTCTGCTCCGGGCG
         C2-TC  TTTCGGGTCCCAACATATGCGCTCTGCCGCAGATGCGTCACAGAAGGTCTGCTCCGGGCG
       C2-NFSgF  TTTCGGGTCCCAACGTATACGCTCTACCGCGGATGCGTCACAGAAGGTCTGCTCCGGGCG Sbescii    TTGGTGCACAAGTACATGATCCCAACCTTTCACTTTCATTTCGCGCTCGGGTTTGACACC
   C2-TC-Orchid  TTGGTGCACAAGTACATGATCCCAACCTTTCACTTTCATTTCGCGCTCGGGTTTGACACC
         C2-TC  TTGGTGCACAAGTACATGATCCCAACCTTTCACTTTCATTTCGCGCTCGGGTTTGACACC
       C2-NFSgF  TCGGTGCACAAGTACATGTTCCCGACCTTTCACTTTCATTACGCGTCCGGGTTTGACACC Sbescii    CAAACACTCGCGCACATGTTAGACTCCTTGGTCCGTGTTTCAAGACGGGTCGCTTAAGGC
   C2-TC-Orchid  CAAACACTCGCGCACATGTTAGACTCCTTGGTCCGTGTTTCAAGACGGGTCGCTTAAGGC
         C2-TC  CAAACACTCGCGCACATGTTAGACTCCTTGGTCCGTGTTTCAAGACGGGTCGCTTAAGGC
       C2-NFSgF  CAAACACTCGCGCACATGTTAGACTCCTTGGTCCGTGTTTCAAGACGGGTCGCTTAAAGC Sbescii    CATTATGCCAGCATCCTAAGCGCGTACCGAGGGCGCGAACCCCGGCCAAAAGGCGCGCTG
   C2-TC-Orchid  CATTATGCCAGCATCCTAAGCGCGTACCGAGGGCGCGAACCCCGGCCAAAAGGCGCGCTG
         C2-TC  CATTATGCCAGCATCCTAAGCGCGTACCGAGGGCGCGAACCCCGGCCAAAAGGCGCGCTG
       C2-NFSgF  CATTATGCCAGTGTCCTAAGCACGTACCGAGGGCGCGAACCCCGGCCAAAAGGCGTGCTG Sbescii    CGTTCCTCAGTCCCAACTGAAGTATACAACAAGGGGTTATAACACTGCCCGAAGGCAGCC
   C2-TC-Orchid  CGTTCCTCAGTCCCAACTGAAGTATACAACAAGGGGTTATAACACTGCCCGAAGGCAGCC
         C2-TC  CGTTCCTCAGTCCCAACTGAAGTATACAACAAGGGGTTATAACACTGCCCGAAGGCAGCC
       C2-NFSgF  CATTCCTCGATCCCAACTGAGACATACAACAAGGGGCTATAACACTGCCCGAAGACAGCC Sbescii    ACCTCCCCAAGCCTTTCTCCTCCAGTCGAAACTGACGCTGACCCATCCTACGGAAAGTA
   C2-TC-Orchid  ACCTCCCCAAGCCTTTCTCCTCCAGTCGAAACTGACGCTGACCCATCCTACGGAAAGTA
         C2-TC  ACCTCCCCAAGCCTTTCTCCTCCAGTCGAAACTGACGCTGACCCATCCTACGGAAAGTA
       C2-NFSgF  ACATTCCCCAAGCCTTTTTCCCTCAATCGAAATCGACACTGACCCGTCGGACAGGAAATA Sbescii    CACCAGGCAGAAGCCAGGCTGAGTTCCGCAAGATGCGACTGACCTCAAACGCTTCCCTTT
   C2-TC-Orchid  CACCAGGCAGAAGCCAGGCTGAGTTCCGCAAGATGCGACTGACCTCAAACGCTTCCCTTT
         C2-TC  CACCAGGCAGAAGCCAGGCTGAGTTCCGCAAGATGCGACTGACCTCAAACGCTTCCCTTT
       C2-NFSgF  CACCAAGCAGAAGCAAGGCTGAATCCCGCCAGACGTGACTGACTCCAAACGCTTCCCTTT Sbescii    CAACAATTTCACGTACTGTTTCACTCTCTTTCCAAAGTGCTTTTCATCTTTCCCTCACGG
   C2-TC-Orchid  CAACAATTTCACGTACTGTTTCACTCTCTTTCCAAAGTGCTTTTCATCTTTCCCTCACGG
         C2-TC  CAACAATTTCACGTACTGTTTCACTCTCTTTCCAAAGTGCTTTTCATCTTTCCCTCACGG
       C2-NFSgF  CAACAATTTCACGTACTGTTTCACTCTCTTTCCAAAGTGCTTTTCATCTTTCCCTCACGG Sbescii    TACTTGTTCGCTATCGGTCTCTCGCCAATATTTA
   C2-TC-Orchid  TACTTGTTCGCTATCGGTCTCTCGCCAATATTTA
         C2-TC  TACTTGTTCGCTATCGGTCTCTCGCCAATATTTA
       C2-NFSgF  TACTTGTTCGCTATCGGTCTCTCGCCAATATTTA
```

Fig. 8B
S vermifera
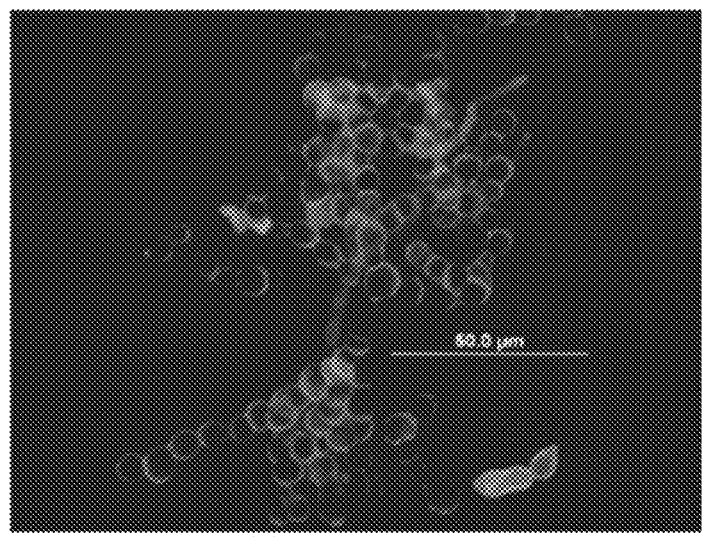
S bescii
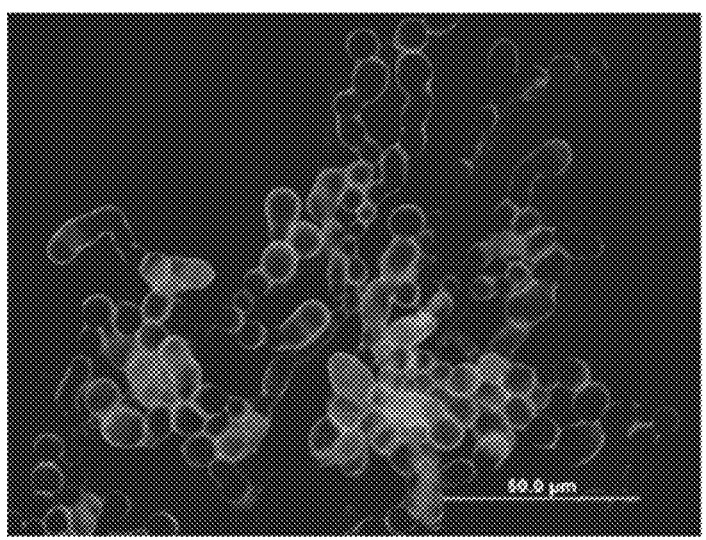

Fig. 8C
S vermifera
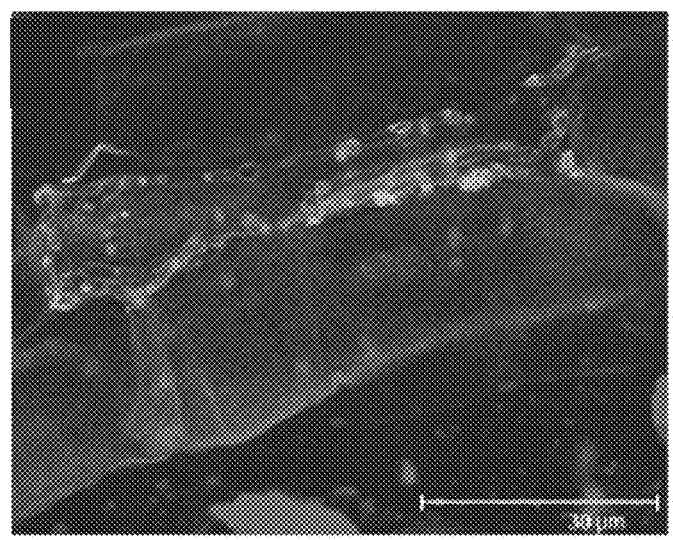
S bescii
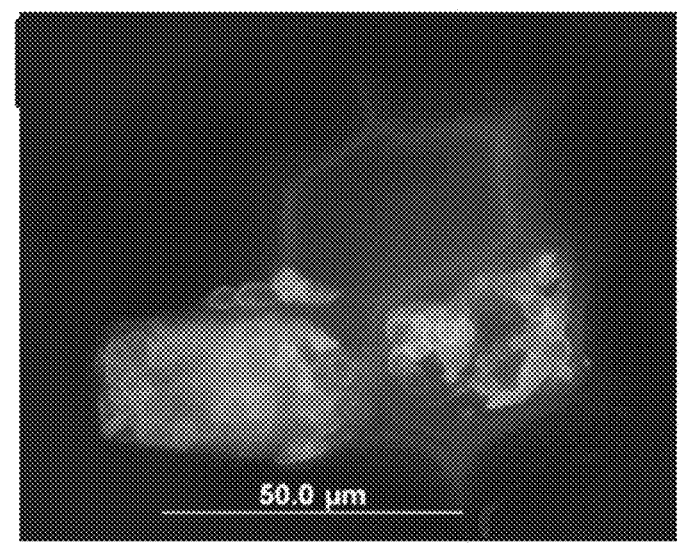

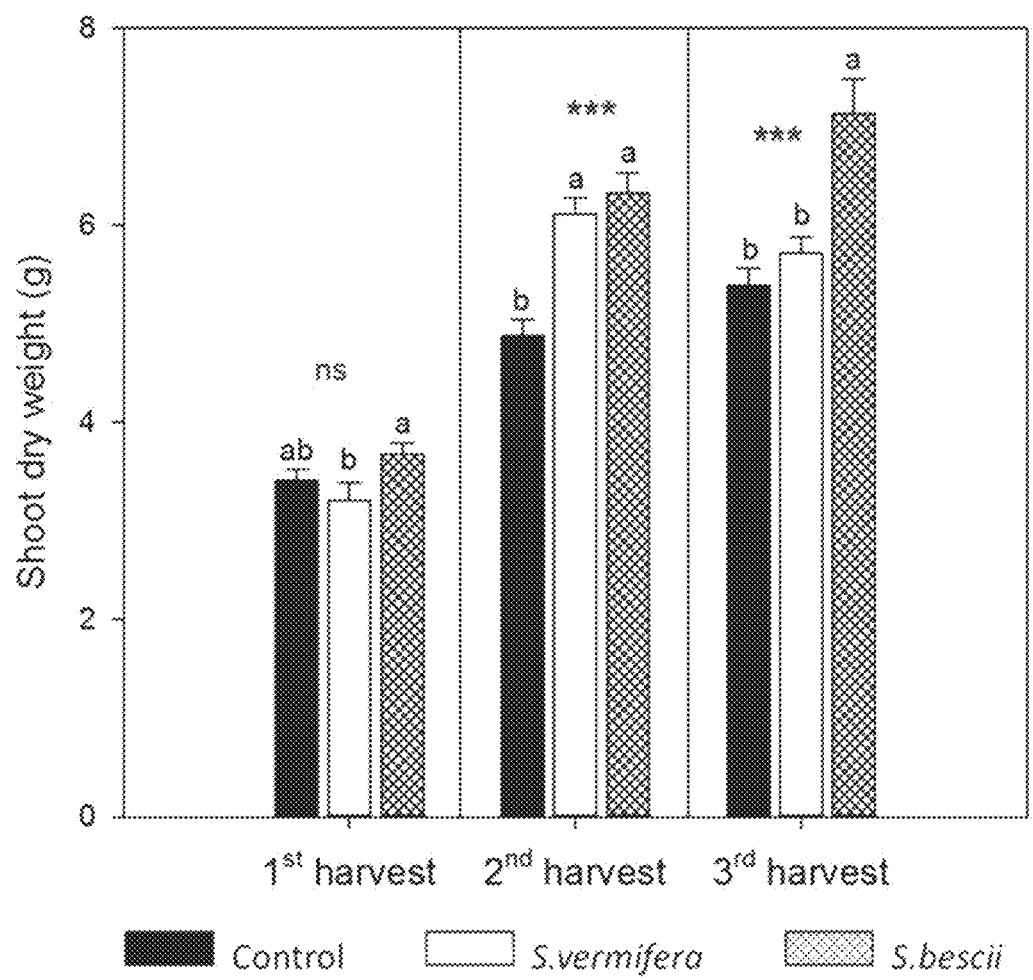

SEQUENCE LISTING

```
<160> NUMBER OF SEQ ID NOS: 22

<210> SEQ ID NO 1
<211> LENGTH: 698
<212> TYPE: DNA
<213> ORGANISM: Serendipita vermifera
<220> FEATURE:
<223> OTHER INFORMATION: ssp. bescii

<400> SEQUENCE: 1
cttggtcatt tagaggaagt aaaagtcgta acaaggtttc cgtaggtgaa cctgcggaag      60
gatcattaac gaatctaaag tcgatgcgtt gtgctggtgg caacacatgt gcacgcgtgt     120
cgcatacatc cacacacctg tgaaccytag actctgtggt cgatcgaacg cccggactcg     180
tccgtcgcrt gtggggactt trtgtcctcc gttcgcccag ggtaattttt acatacgccg     240
aatgtgatag aatgtatctg tgcataacgc gcaactaata caactttcaa caacggatct     300
cttggctctc gcatcgatga agaacgcagc gaaatgcgat aagtaatgtg aattgcagaa     360
ttcagtgaat catcgaatct tcgaacgcac cttgcgccct ttggtattcc gaagggcacg     420
cccgtttgag tgtcattgta atctcacctc cacggtttct tatcgtggtc gtggatctgg     480
acgtygtcgg cttgtcgacc cgtctgaaat gtatgagtgt accctgccgt gcagcgtatc     540
tggtgtgata agcatcttca ccggagtaat gcctcctttg gcgcgtctgt ggtgtgggct     600
ctgcgcttcg aaccgtcctc acaggacaat ctttgacrat ttgacctcag atcgggcggg     660 actcccgct gaacttaagc atatcaataa gcggagga                              698

<210> SEQ ID NO 2
<211> LENGTH: 61
<212> TYPE: DNA
<213> ORGANISM: Serendipita vermifera
<220> FEATURE:
<223> OTHER INFORMATION: ssp. bescii

<400> SEQUENCE: 2
ggtcgatcga acgcccggac tcgtccgtcg crtgtgggga ctttrtgtcc tccgttcgcc      60
c                                                                      61

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gactcaacac gggaaactc                                                   19

<210> SEQ ID NO 4
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 4
gcccactaga aactctcacc                                              20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttcttagag ggactgtcag ga                                           22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
attcgcttta ccgcacaagg c                                            21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgagtgtcat tgtaatctca c                                            21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtccgtgtt tcaagacgg                                               19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagaccaaac tccggtgaaa                                              20

<210> SEQ ID NO 10
<211> LENGTH: 21
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 10
tgagcgtcat tgtaatctca c                                              21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actttgtgtc ctccgttcg                                                 19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcctccgctt attgatatgc                                                20

<210> SEQ ID NO 13
<211> LENGTH: 634
<212> TYPE: DNA
<213> ORGANISM: Serendipita vermifera
<220> FEATURE:
<223> OTHER INFORMATION: ssp. bescii

<400> SEQUENCE: 13
ggttcgatta gtctttcgcc cctatacccca aatttgacga tcgatttgca cgtcagaatc    60
gctacgagcc tccaccagag tttcctctgg cttcacccta ttcaggcata gttcaccatc   120
tttcgggtcc caacatatgc gctctgccgc agatgcgtca cagaaggtct gctccgggcg   180
ttggtgcaca agtacatgat cccaaccttt cactttcatt tcgcgctcgg gtttgacacc   240
caaacactcg cgcacatgtt agactccttg gtccgtgttt caagacgggt cgcttaaggc   300
cattatgcca gcatcctaag cgcgtaccga gggcgcgaac cccggccaaa aggcgcgctg   360
cgttcctcag tcccaactga agtatacaac aagggggttat aacactgccc gaaggcagcc   420
acctccccca agcctttctc ctccagtcga aactgacgct gacccatcct acggaaagta   480
caccaggcag aagccaggct gagttccgca agatgcgact gacctcaaac gcttcccttt   540
caacaatttc acgtactgtt tcactctctt tccaaagtgc ttttcatctt tccctcacgg   600
tacttgttcg ctatcggtct ctcgccaata ttta                                634

<210> SEQ ID NO 14
<211> LENGTH: 634
<212> TYPE: DNA
<213> ORGANISM: Serendipita sp.

<400> SEQUENCE: 14
ggttcgatta gtctttcgcc cctatacccca aatttgacga tcgatttgca cgtcagaatc    60
gctacgagcc tccaccagag tttcctctgg cttcacccta ttcaggcata gttcaccatc   120
tttcgggtcc caacatatgc gctctgccgc agatgcgtca cagaaggtct gctccgggcg   180

```
ttggtgcaca agtacatgat cccaaccttt cactttcatt tcgcgctcgg gtttgacacc      240
caaacactcg cgcacatgtt agactccttg gtccgtgttt caagacgggt cgcttaaggc      300
cattatgcca gcatcctaag cgcgtaccga gggcgcgaac cccggccaaa aggcgcgctg      360
cgttcctcag tcccaactga agtatacaac aaggggttat aacactgccc gaaggcagcc      420
acctccccca agcctttctc ctccagtcga aactgacgct gacccatcct acggaaagta      480
caccaggcag aagccaggct gagttccgca agatgcgact gacctcaaac gcttcccttt      540
caacaatttc acgtactgtt tcactctctt tccaaagtgc ttttcatctt tccctcacgg      600
tacttgttcg ctatcggtct ctcgccaata ttta                                  634
```

<210> SEQ ID NO 15
<211> LENGTH: 634
<212> TYPE: DNA
<213> ORGANISM: Serendipita sp.

<400> SEQUENCE: 15

```
ggttcgatta gtctttcgcc cctataccca aatttgacga tcgatttgca cgtcagaatc      60
gctacgagcc tccaccagag tttcctctgg cttcacccta ttcaggcata gttcaccatc      120
tttcgggtcc caacatatgc gctctgccgc agatgcgtca cagaaggtct gctccgggcg      180
ttggtgcaca agtacatgat cccaaccttt cactttcatt tcgcgctcgg gtttgacacc      240
caaacactcg cgcacatgtt agactccttg gtccgtgttt caagacgggt cgcttaaggc      300
cattatgcca gcatcctaag cgcgtaccga gggcgcgaac cccggccaaa aggcgcgctg      360
cgttcctcag tcccaactga agtatacaac aaggggttat aacactgccc gaaggcagcc      420
acctccccca agcctttctc ctccagtcga aactgacgct gacccatcct acggaaagta      480
caccaggcag aagccaggct gagttccgca agatgcgact gacctcaaac gcttcccttt      540
caacaatttc acgtactgtt tcactctctt tccaaagtgc ttttcatctt tccctcacgg      600
tacttgttcg ctatcggtct ctcgccaata ttta                                  634
```

<210> SEQ ID NO 16
<211> LENGTH: 634
<212> TYPE: DNA
<213> ORGANISM: Serendipita sp.

<400> SEQUENCE: 16

```
ggttcgatta gtctttcgcc cctataccca aatttgacga tcgatttgca cgtcagaatc      60
gctacgagcc tccaccagag tttcctctgg cttcacccta ttcaggcata gttcaccatc      120
tttcgggtcc caacgtatac gctctaccgc ggatgcgtca cagaaggtct gctccgggcg      180
tcggtgcaca agtacatgtt cccgaccttt cactttcatt acgcgtccgg gtttgacacc      240
caaacactcg cgcacatgtt agactccttg gtccgtgttt caagacgggt cgcttaaagc      300
cattatgcca gtgtcctaag cacgtaccga gggcgcgaac cccggccaaa aggcgtgctg      360
cattcctcga tcccaactga gacatacaac aaggggctat aacactgccc gaagacagcc      420
acattcccca agccttttc cctcaatcga aatcgacact gacccgtcgg acaggaaata      480
caccaagcag aagcaaggct gaatcccgcc agacgtgact gactccaaac gcttcccttt      540
caacaatttc acgtactgtt tcactctctt tccaaagtgc ttttcatctt tccctcacgg      600
tacttgttcg ctatcggtct ctcgccaata ttta                                  634
```

<210> SEQ ID NO 17

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcgaacgcc cggactcg                                                   18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctatcctga gggaaacttc                                                 20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttggtcatt tagaggaagt aa                                              22

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccgtaggtg aacctgcgg                                                  19

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgactgtag gatctacctg acgg                                            24

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccgcacaagg ctgataa                                                    17
```

SYMBIONT FOR ENHANCEMENT OF PLANT PERFORMANCE

CROSS-REFERENCE TO RELATED APPLICATIONS

The present application is a Continuation of International Application No. PCT/US17/35844 filed on Jun. 2, 2017 which claims the benefit of U.S. Provisional Application No. 62/345,766, filed on Jun. 4, 2016 which are both herein incorporated by reference in their entirety.

STATEMENT OF GOVERNMENT INTEREST

This invention was made with Government support under DOE Prime Contract #DEAC05OOOR22725 awarded by the Department of Energy. The Government has certain rights in this invention.

SEQUENCE LISTING

The instant application contains a Sequence Listing which has been filed electronically in ASCII format and is hereby incorporated by reference in its entirety. Said ASCII copy, created on Jun. 2, 2017, is named 17-21003-WO_SL.txt and is 8,913 bytes in size.

BACKGROUND

Endophytes are typically fungal or bacterial organisms that live within or on plants. Fungal symbionts, such as mycorrhiza or certain clavicipitaceous foliar endophytes, survive within various host plant tissues, often colonizing the inter-cellular spaces of host's leaves, stems, flowers, or roots. These symbiotic endophyte-host relationships can provide fitness benefits to the host plant, such as enhancement of nutrient uptake or chemical defense from potential herbivores. Root-colonizing mycorrhizae often survive on photosynthetic carbohydrates from the plant, and in return, aid in the solubilization and uptake of water and minerals to the host, which can lead to the promotion of seed germination and plant growth. Additionally, the association of a fungal endophyte with a host plant often provides protection from pathogens or tolerance to a variety of biotic and abiotic stresses, such as insect infestation, grazing, water or nutrient deficiency, heat stress, salt of aluminum toxicity, and freezing temperatures. Host growth and fitness promotion and protection are thought to be achieved through multiple beneficial properties of the endophyte-host association. For instance, the endophytic organisms may produce growth-regulating substances to induce biomass production and alkaloids or other metabolites that have anti-insect and anti-herbivore properties. Additionally, fungal endophytes may directly suppress or compete with disease causing microbes, protecting the plant from potential pathogens.

Endophytic relationships between non-pathogenic fungi and host plants are of agricultural interest, particularly in plants that serve as sources for food, feed, fiber and ornamentals for a global population. Whether monocots (e.g., corn, wheat, switchgrass, rice) or dicots (e.g., legumes, tomato, cotton), there is a need to improve one or more of the following: plant biomass and/or output yields, overall plant health and productivity, and promotion of host plant protection from and tolerance to biotic and abiotic stresses.

SUMMARY

The present disclosure provides a novel endophyte, *Serendipita vermifera* ssp. *bescii* ("*S. bescii*"), uses thereof and methods incorporating the use thereof for enhancement of plant performance. The present disclosure also provides methods for detecting the presence of and identifying *S. bescii*.

The *S. bescii* endophyte of the present disclosure comprises a ribosomal DNA (rDNA) sequence comprising the nucleotide sequence of SEQ ID NO: 2. More specifically, the *S. bescii* endophyte of the present disclosure comprises a rDNA sequence comprising the nucleotide sequence of SEQ ID NO: 1 which contains the nucleotide sequence of SEQ ID NO: 2. These sequences are unique to *S. bescii*.

In some embodiments, a composition is provided comprising a carrier material and a *S. bescii* endophyte, wherein the *S. bescii* endophyte comprises a nucleotide sequence of SEQ ID NO: 2. In some embodiments, a composition is provided comprising a fungal endophyte and bentonite clay.

In some embodiments, a method is provided for preparing an inoculum comprising providing particles of a carrier material, adding a fungal culture broth to the particles of the carrier material, adding a *S. bescii* fungal mycelium derived from liquid broth culture to the fungal culture broth and particles of the carrier material, incubating the mixture for a period of time, optionally, drying the mixture, where the *S. bescii* comprises a nucleotide sequence of SEQ ID NO: 2. In some embodiments, a method comprises inoculating a host plant with an inoculum by contacting the host plant with the inoculum comprising a *S. bescii* endophyte comprising the nucleotide sequence of SEQ ID NO: 2 under conditions sufficient to promote colonization of the roots of the host plant by the *S. bescii* endophyte.

In some embodiments, a synthetic combination includes a *S. bescii* endophyte and a host plant, wherein the *S. bescii* endophyte comprises the nucleotide sequence of SEQ ID NO: 2.

In some embodiments, a method for propagating a host plant-*S. bescii* combination comprises obtaining a synthetic combination of a *S. bescii* endophyte and a host plant and vegetatively reproducing the host plant tissue colonized by the *S. bescii* endophyte. In some embodiments, a method for cultivating a plant comprises contacting a plant with a culture filtrate from a *S. bescii* culture.

In some embodiments, a method is provided for identifying a microorganism as *S. bescii* in a sample comprises performing a polymerase chain reaction (PCR) on the sample with primers suitable to amplify the internal transcribed spacer (ITS) region of Serendipitaceae including a 3' portion of the 18S sequence or portion thereof, sequencing the product of the PCR, comparing the sequence obtained to SEQ ID NO: 2 or SEQ ID NO: 1, and determining whether the microorganism is *S. bescii* based on homology between the sequence of the product of the PCR and SEQ ID NO: 2 or SEQ ID NO: 1. In some embodiments, a method for identifying a microorganism as *S. bescii* in a sample comprises performing a PCR on the sample using primers specific for *S. bescii* and determining that the sample contains *S. bescii* if a PCR product is obtained.

In some embodiments, a seed comprises a synthetic combination of a *S. bescii* fungal endophyte and a host plant embryo, wherein the *S. bescii* fungal endophyte comprises the nucleotide sequence of SEQ ID NO: 2. In some embodiments, a seed comprises a seed-coat comprising a *S. bescii* fungal endophyte comprising the nucleotide of SEQ ID NO: 2, wherein the fungal endophyte colonizes a root tissue of the host plant.

In some embodiments a method for colonizing a host plant with a *S. bescii* endophyte is provided which comprises placing bentonite clay particles comprising a *S. bescii* endophyte comprising the nucleotide sequence of SEQ ID NO: 2 in living soil and planting a seed of the host plant in contact with the bentonite clay particles under conditions sufficient for the *S. bescii* endophyte to colonize the roots of the host plant.

Other objects, features and advantages of the present disclosure will become apparent from the following detailed description. It should be understood, however, that the detailed description and specific examples, while indicating specific embodiments of the invention, are given by way of illustration only, since various changes and modifications within the scope of the present disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Some specific example embodiments of the disclosure may be understood by referring, in part, to the following description and the accompanying drawings.

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein.

FIG. 4 depicts the pairwise multiple alignment of D1/D2 rDNA sequences between Serendipitoid sequences detected in switchgrass roots from field (NFSgF) (SEQ ID NO: 16), trap culture (TC) (SEQ ID NO: 15) and from a rhizobox (TC-Orchid) (SEQ ID NO: 14) with *S. bescii* axenic culture (SEQ ID NO: 13).

FIG. 8B shows fluorescent micrographs showing moniloid hyphae stained with WGA-AF® 488 of the axenic cultures of *S. bescii* and *S. vermifera* (MAFF305830) on MMN agar. Scale bar=50.0 μm.

FIG. 8C shows fluorescent micrographs showing the transverse section of colonized swiitchgrass root cells stained with WGA-AF® 488 and propidium iodide, colonized with *S. bescii* or *S. vermifera* (MAFF305830). Scale bar=50.0 μm (*S. bescii*); Scale bar=30.0 μm (*S. vermifera*).

FIG. 11A depicts the forage dry weight under normal watering conditions for winter wheat inoculated with *S. bescii*, *S. vermifera* (MAFF305830) or un-inoculated over three harvests. Bars with different letters indicate a significant different between treatment at $p \leq 0.05$.

DESCRIPTION

Figure 1:
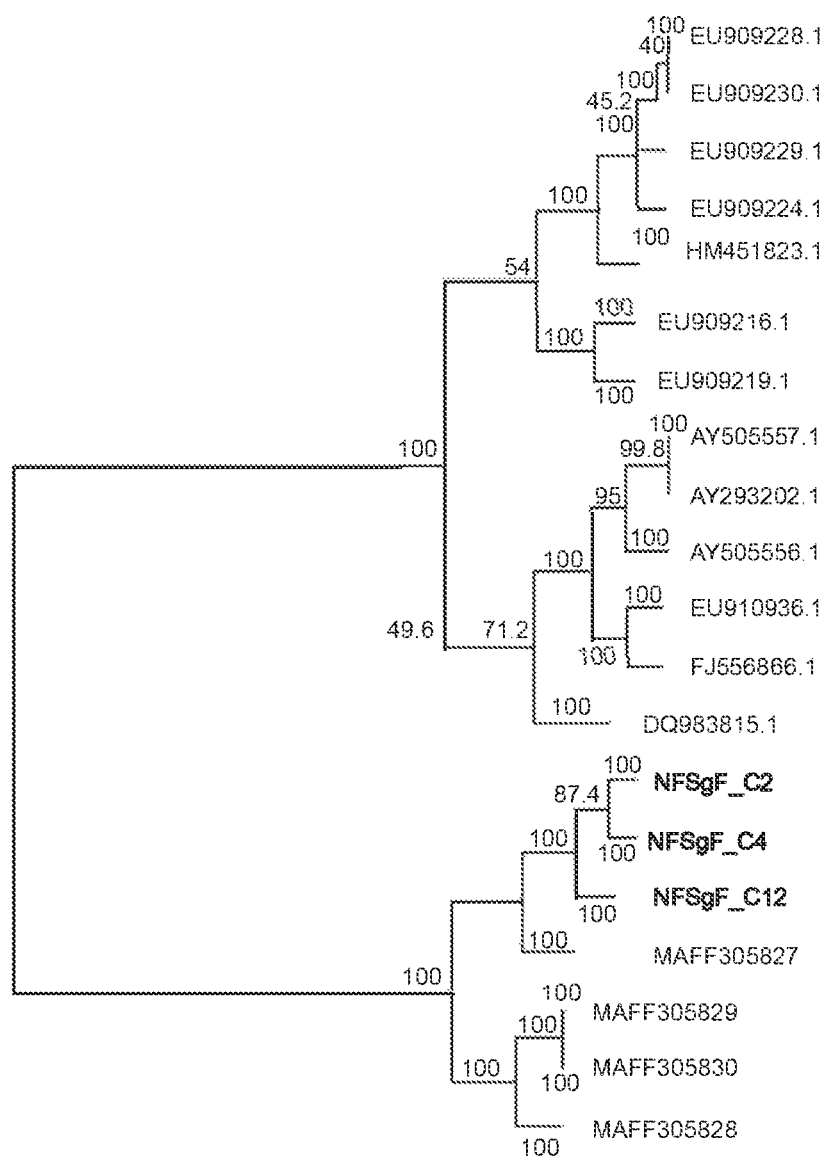
FIG. 1 depicts the phylogenetic relationship between three Serendipitoid sequences detected in switchgrass roots with serendipitoid sequences from GenBank and reference strains of *Serendipita vermifera* (*S. vermifera*) isolated from Australian orchid reconstructed by the UPGMA method for 20 partial 18S/5.8S/partial LSU rDNA sequences (alignment length 750 bp). Numbers are UPGMA bootstrap values based on 500 replicates. The bar indicates substitutions per site.

The present disclosure describes particular embodiments and with reference to certain drawings, but the subject matter is not limited thereto. The drawings described are only schematic and are non-limiting. In the drawings, the size of some of the elements may be exaggerated or distorted and not drawn on scale for illustrative purposes. Where the elements of the disclosure are designated as "a" or "an" in first appearance and designated as "the" or "said" for second or subsequent appearances unless something else is specifically stated.

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Definitions

Certain terminology is used in the following description for convenience only and is not limiting. Certain words used herein designate directions in the drawings to which reference is made. Unless specifically set forth herein, the terms "a," "an" and "the" are not limited to one element, but instead should be read consistent with the meaning of "one or more," "at least one," and "one or more than one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about", when used with a numerical value, is intended to include +/−10%. For example, if a number of amino acids is identified as about 200, this would include 180 to 220 (plus or minus 10%).

Unless otherwise defined, all technical and scientific terms used herein have the same meaning as commonly understood by one of ordinary skill in the art.

As used herein, the term "biomass" means the total mass or weight, at a given time, of a plant or population plants, usually given as weight per unit area. The term may also refer to all of the plants or species in the community ("community biomass").

As used herein, the term "culture filtrate" means broth or media obtained from cultures inoculated with a strain of fungi and allowed to grow. The media is typically filtered to remove any suspended cells leaving the nutrients, hormones or other chemicals.

As used herein, the term "endophyte" refers to an organism capable of living in or on a plant or plant cell. An endophyte may refer to a fungal organism that may confer an increase in yield, biomass, resistance or fitness in its host plant. Fungal endophytes may occupy the intra-cellular, inter-cellular or extra-cellular spaces of plant tissue, including the leaves, stems, flowers, or roots.

As used herein, the term "host plant" means a plant which an endophytic fungi can colonize.

As used herein, the term "increased yield" refers to an increase in seed or fruit weight, seed or fruit size, output per plant, output per unit area (e.g., seeds, fruit, or weight of seeds or fruit per acre), bushels per acre, tons per acre, kilo per hectare. Additionally, the term may refer to an increase in plant height, number of internodes, grain side, amount of tillers, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other yield traits that can affect yield include, efficiency of germination (including germination in stressed conditions), growth rate (including growth rate in stressed conditions), composition of seed (e.g., starch, oil, protein) and characteristics of seed fill. Yield may be increased by at least 5%, 10%, 15%, 20%, 30%, 50%, 75%, 100% or more as compared to control plants under the same conditions.

As used herein, the term "phenotype" refers to detectable characteristics of a cell or organism, which characteristics are a manifestation of gene expression.

As used herein, the term "regeneration" refers to the process of growing a plant from a plant cell (e.g., plant protoplast, callus or explant).

As used herein, the term "synthetic combination" refers to a combination (also termed a "symbiotum") of a host plant and an endophyte which arises as the result of human intervention and which is not found in nature. The combination may be achieved, by way of example but not limitation, by artificial inoculation, application or other infection of a host plant, whether a monocot or dicot plant, or host plant tissues with an endophyte.

The present disclosure generally relates to a novel endophyte, S. bescii, uses thereof and methods incorporating the use thereof for enhancement of plant performance. The present disclosure also provides methods for detecting the presence of and identifying S. bescii.

The basidiomycetous species Serendipita vermifera is characterized primarily as an asexually reproducing mycorrhize isolated from orchids, for instance Australian orchids. Phylogenetic analysis has placed these endophytes within the order Serendipitaceae, based upon a maximum likelihood of phylogenetic analysis of nuclear rDNA encoding the ribosomal large subunit.

S. vermifera stains have also been isolated from orchid host plants and are known to one of skill in the art. The S. bescii endophyte of the present disclosure is a novel strain of S. vermifera. The S. bescii endophyte comprises an ITS sequence of SEQ ID NO: 1 which includes an indel domain of SEQ ID NO: 2, both of which are unique to the S. bescii endophyte. Throughout this disclosure, the S. bescii endophyte can be referred to as Serendipita vermifera ssp. bescii, Serendipita bescii, Sebacina vermifera ssp. bescii, Sebacina bescii and S. bescii. It should be understood that all of these terms are equivalent and refer to the same endophyte, which is a strain of the type deposited with the American Type Culture Collection (ATCC) under designation number PTA-124559 and Strain NFPB0129, samples of which have been deposited by The Noble Research Institute with the ATCC at 10801 University Blvd., Manassas, Va. 20110 United States of America on Nov. 10, 2017 in conformance with the Budapest Treaty on the International Recognition of the Deposit of Microorganisms for the Purposes of Patent Procedure.

S. bescii colonizes the roots of plants and forms hyphal networks on and inside the root cells and inter-cellular spaces. These hyphae extend into the nearby rhizosphere and may form chlamydospores (survival structures) and may persist in soil upon decay of roots or root hairs. S. bescii strains can, therefore, be isolated from soil or host plants which are colonized with the fungal endophyte using isolation methods known in the art.

It has been found that colonization of a host plant by S. bescii can result in plant growth, such as an increase in biomass of 10% or more. Yield increases were also observed across multiple plant species, including switchgrass (Panicum virgatum), winter wheat (Triticum aestivum) and alfalfa (Medicago sativa). Each of these plants have the potential for a substantial economic impact in cultivation and production. Thus, S. bescii colonization of such plants has the potential to increase the overall productivity and commercial value of host plants, which produces a substantial and unexpected benefit. For example, switchgrass has been identified as a candidate for the production of ethanol or advanced biofuels. As the future need for renewable fuel alternatives increases, so does the need for more products crops and methods to increase the yield of candidate monocots, such as grasses. It has also been found that S. bescii can act as a soil conditioner by metabolizing organic matter in soil. Without being bound to theory, it is believed that the capacity of S. bescii to metabolize organic matter is responsible, at least in part, for its improved effects on host plants. Without being bound to theory, it is believed that the S. bescii genome includes a full complement of genes encoding cellulolytic enzymes and also includes urea transporters which may be responsible for these effects.

In addition to the increased yields observed, the endophytic S. bescii/host plant combination has the potential to increase other attributes including, but not limited to, seed germination, plant fitness, and stress tolerance. These benefits can also contribute to increased biomass and/or seed (or fruit) production.

In some embodiments, a host plant infected with S. bescii displays increased biomass, vigor, stress tolerance, and/or productivity relative to a host plant of the same genotype that lacks the endophyte, when grown under substantially similar conditions. In some embodiments, the host plant can be an ornamental or used for food, feed or fiber and can be artificially inoculated with S. bescii. The combination of the host plant and S. bescii can provide protection to the host plant, in some instances a crop plant, from biotic stresses such as insect infestation, nematode infestation and/or herbivore grazing and/or abiotic stresses such as water deficiency, nutrient deficiency, heat stress, salt toxicity, aluminum toxicity, heavy metal toxicity and freezing temperatures. In some embodiments, the combination of the host plant and *S. bescii* can be more tolerant of stresses compared to a host plant of the same genotype lacking the *S. bescii* endophyte. Such stresses can include, by way of example but not limitation, biotic stress, pest stress, or insect stress. Examples of biotic stress include, but are not limited to, stress caused by a mammalian or insect herbivore or microbial pathogen (e.g., nematode, fungus, bacteria or virus).

In some embodiments, the present disclosure provides a synthetic combination of a *S. bescii* endophyte and a host plant, wherein the *S. bescii* endophyte comprises the nucleotide sequence of SEQ ID NO: 2. In some embodiments, the *S. bescii* endophyte comprises the nucleotide sequence of SEQ ID NO: 1. Host plants of the present disclosure can be understood to include plants at all stages of development, including by way of example but not limitation, plants, seedlings and seeds. In some embodiments the synthetic combination can further include a carrier material which is impregnated or coated with the *S. bescii* endophyte. In some embodiments, the carrier forms a seed coat on a seed. In an embodiment, a synthetic combination of a *S. bescii* endophyte and a host plant, comprises the *S. bescii* endophyte in a seed coat which coats the seed. In some embodiments a seed comprises a *S. bescii* endophyte. In an embodiment, the *S. bescii* endophyte is integrated into or onto the seed-coat of the seed. In some embodiments, a seed comprises a synthetic combination of a *S. bescii* fungal endophyte and a host plant embryo. In some embodiments, a seed comprises a seed-coat comprising a *S. bescii* fungal endophyte, wherein the fungal endophyte colonizes a root tissue of the host plant.

In some embodiments, the present disclosure provides a composition comprising a carrier material and a *S. bescii* endophyte, wherein the *S. bescii* endophyte comprises the nucleotide sequence of SEQ ID NO: 2. In some embodiments, the *S. bescii* endophyte comprises the nucleotide sequence of SEQ ID NO: 1. In some embodiments, the carrier material is impregnated or coated with the *S. bescii* endophyte.

In an embodiment, a method is provided for preparing an inoculum which includes providing particles of a carrier material, adding a fungal culture broth to the particles of the carrier material; and adding a *S. bescii* fungal mycelium derived from liquid broth culture to the fungal culture broth and particles of the carrier material followed by incubating the mixture of the *S. bescii* fungal mycelium derived from liquid broth culture, fungal culture broth and particles of the carrier material for a period of time. The mixture can then be dried. In some embodiments, the steps of adding a fungal culture broth to the particles of the carrier material and adding the *S. bescii* fungal mycelium derived from liquid broth culture to the fungal culture broth can be combined as a single step by providing a *S. bescii* culture in fungal culture broth to the particles of the carrier material. In some embodiments, the mixture can be shaken while incubating the mixture. The shaking can be performed at regular intervals during the period of time, such as, by way of example but not limitation, weekly. The period of time for incubation can be any period of time sufficient for growth of the *S. bescii* endophyte and/or to impregnate or coat the particles of carrier with the *S. bescii* endophyte. By way of example but not limitation, the period of time can be 6 weeks or 8 weeks. In some embodiments, prior to adding the particles of the carrier material, the carrier material can sieved. By way of example but not limitation, sieving can be performed using a mesh size of 10 (2 mm). In certain aspects, the fungal culture broth and/or the particles of carrier material are sterile before adding the fungal mycelium derived from liquid broth culture. The drying step can be performed by any method, preferably a sterile method to prevent contamination of the carrier particles. In an embodiment, the drying can be air drying. The drying time can be any time sufficient to result in dry particles of carrier. In an embodiment, the drying can be overnight. In some embodiments, a composition comprises a fungal endophyte and a bentonite clay. In some aspects, the fungal endophyte is *S. bescii*.

In some embodiments, a method is providing for inoculating a host plant with an inoculum comprising a *S. bescii* endophyte by contacting the host plant with the inoculum under conditions sufficient to promote colonization of the roots of the host plant by the *S. bescii* endophyte. This method can result in colonization of the host plant by the *S. bescii* endophyte. Methods for inoculating can include, by way of example but not limitation, inoculation, infection, grafting and combinations thereof. The inoculum can be any composition which can provide the *S. bescii* endophyte to the host plant. By way of example, but not limitation, the inoculum can include a carrier material impregnated or coated with the *S. bescii* endophyte. In some embodiments, the inoculum can include portions of a plant infected with the *S. bescii* endophyte. In an embodiment, the portions of the plant infected with the *S. bescii* endophyte can be root cuttings. In an embodiment, the inoculum is a culture of *S. bescii*. In some embodiments, the inoculum comprises bentonite clay impregnated or coated with the *S. bescii* endophyte. In some embodiments, the inoculum is provided in an effective amount to result in colonization of the host plant by the *S. bescii* endophyte. In certain aspects, the host plant is a monocot. In some aspects, the host plant is a dicot. In certain aspects, the host plan can be a seed. In some embodiments, the inoculating is performed by contacting the inoculum with a portion of the host plant. In some aspects, the portion of the host plant is the roots of the host plant. In some embodiments, the inoculum can be sprayed onto living soil before planting the host plant or seed in the living soil. In some embodiments, the inoculating is performed by adding the inoculum to living soil in contact with the seed of a host plant. In some embodiments, the inoculating is performed by adding the inoculum to living soil in contact with the roots of the host plant. In an embodiment, the inoculum is added to living soil prior to planting a seed in the soil.

The inoculation of the host plant can be performed at any time during the plant life cycle. In some embodiments, the inoculum is added to living soil before planting the host plant. In some embodiments, the inoculum is added to the host plant simultaneously with planting the plant in living soil. For example, in an embodiment, seeds can be mixed with the inoculum, such as bentonite clay particles impregnated with the *S. bescii* endophyte and planted in living soil. In some embodiments, this can be accomplished by a spray application or aggregating the seeds with the inoculum. In some embodiments, the *S. bescii* endophyte can be coated on a carrier. In some embodiments, the inoculum is added to the host plant in living soil after germination of the host plant. For example, in an embodiment, alfalfa can be supplemented with phosphorous after germination, at which time the inoculum can be added to colonize the alfalfa host plant.

It should also be understood, that inoculation of a host plant or seed can be performed in artificial media such that the host plant becomes colonized by the *S. bescii* endophyte. Such a plant can be subsequently planted in living soil. In an embodiment, a composition comprising bentonite clay and *S. bescii* can be placed in soil followed by planting a seed under conditions sufficient to promote colonization of the roots of the host plant.

It should be understood that the carrier material of any of the foregoing embodiments can include any material which can be impregnated or coated with the *S. bescii* endophyte and which does not prevent growth of the *S. bescii* endophyte. In some embodiments, the carrier material is a porous material. In some aspects, the carrier material is an inorganic matrix material. In some aspects, the carrier material is charcoal. In certain aspects, the inorganic matrix material is bentonite clay. In some embodiments, the carrier forms a seed coat on a seed. In an embodiment, a synthetic combination of a *S. bescii* endophyte and a host plant, comprises the *S. bescii* endophyte in a seed coat which coats the seed.

In some embodiments, a method is provided for propagating a synthetic combination of a host plant and *S. bescii* endophyte by vegetative reproduction. Vegetative propagation of the plant allows for propagation of the combination since fungal propagules (e.g., mycelia, conidia and chlamydospores) are present in or in plant tissue and may infect the plant tissue. In some embodiments, a method of cultivating a plant comprises contacting a plant with a culture filtrate from a *S. bescii* culture. In some embodiments, this method results in the plant having enhanced root growth, more tillers, enhanced total biomass, or enhanced seed (or fruit) yield or germination relative to a plant of the same genotype that lacks the filtrate, when grown under substantially the same conditions. In some embodiments, this method results in the plant having improved tolerance to biotic stresses, pest stress, insect stress, abiotic stress and water deficit stress.

In some embodiments, the synthetic combination of the *S. bescii* endophyte with a host plant can positively influence the agronomic qualities of the host plant. Such agronomic qualities can include, but are not limited to, increased root and/or shoot biomass, increased tillering, increased root mass, increased flowering, increased seed yield, and enhanced resistance to biotic and/or abiotic stresses. In some embodiments, the agronomic qualities are increased compared to plants of the same genotype grown under the same conditions but lacking the *S. bescii* endophyte. The combination of *S. bescii* and a host plant can protect the host plant from biotic and/or abiotic stresses which can include, by way of example but not limitation, drought (water deficit), cold, heat stress, nutrient deficiency, salt toxicity, aluminum toxicity, heavy metal toxicity, grazing by herbivores, insect infestation, nematode infection and fungal infection. The combination can also improve a host plant's ability to resist, tolerate and/or overcome pathogens. For example, the enhanced resistance which is provided by the endophyte can protect the host plant from subsequent infection by other fungal diseases, such as root rot, powdery mildew, *Fusarium* blight, *Pythium* blight, leaf spot, rust and snow mold. This resistance can allow for improved biomass or seed yield relative to plants not colonized by the *S. bescii* endophyte.

In some embodiments, a method is provided for identifying a microorganism as *S. bescii* in a sample. The method includes the steps of performing a polymerase chain reaction (PCR) on the sample using primers suitable to amplify an internal transcribed spacer (ITS) region of Serendipitaceae including a 3' portion of the 18S sequence or portion thereof, sequencing the product, if any, obtained, and comparing the sequence obtained with SEQ ID NO: 1 and/or SEQ ID NO: 2 to determine whether the microorganism is *S. bescii* based on homology between the sequence of the product of the PCR and SEQ ID NO: 1 and/or SEQ ID NO: 2. In an embodiment, the primers have the nucleotide sequences of SEQ ID NO: 19 (ITS1F) and SEQ ID NO: 12 (ITS4), respectively. In some embodiments, the PCR is a nested PCR.

In some embodiments, a method for identifying a microorganism as *S. bescii* in a sample can include the steps of performing a PCR on the sample using primers specific for *S. bescii* and determining if the sample contains *S. bescii* if a PCR product is obtained. In an embodiment, the *S. bescii* specific primers have nucleotide sequences of SEQ ID NO: 11 and SEQ ID NO: 12, respectively.

In some embodiments, a method is provided for identifying a microorganism as *S. bescii* in a sample comprising performing a PCR on the sample with primers suitable to amplify the ITS region of the ribosomal DNA of Serendipitaceae. It will be appreciated by one of ordinary skill in the art that different combinations of primers can amplify any region of DNA comprising the ITS region and 3' portion of the 18S sequence of the ribosomal DNA or a portion thereof. It will also be appreciated that the PCR product using different combinations of primers can include all or a portion of SEQ ID NO: 1 and SEQ ID NO: 2 or a corresponding portion thereof which can be analyzed to identify *S. bescii* in a sample by comparison to SEQ ID NO: 1 and/or SEQ ID NO: 2.

It should be understood that any method for detecting the presence of specific nucleic acid and/or amino acid sequences associated with the presence of *S. bescii* can be used to determine whether an endophyte is *S. bescii* and/or whether a sample contains *S. bescii*. Such methods can include isolation of total DNA from tissues of a potential plant-endophyte combination, followed by PCR, or alternatively, Southern blotting, western blotting or other methods known in the art. In addition, biochemical methods such as ELISA, HPLC, TLC and/or fungal metabolite assays can be utilized. Methods of identification can also include microscopic analysis, such as root staining, or culturing methods, such as grow out tests or other methods known in the art. In some embodiments, the roots of a potential host plant-endophyte combination can be stained with fungal specific stains, such as WGA-AF® 488 and microscopically assayed to determine fungal root associates.

The *S. bescii* endophyte of the present disclosure may be introduced into any type of plant, including both monocots and dicots. By way of example but not limitation, such monocots include wheat (*Triticum aestivum*), durum wheat (*Triticum turgidum* ssp. *durum*), tall wheatgrass (*Thinopyrum ponticum*), western wheatgrass (*Pascopyrum smithii*), maize (*Zea mays*), rice (*Oryza sativa*), sorghum (*Sorghum bicolor*), onion (*Allium cepa*), asparagus (*Asparagus officinalis*), miller (*Gramene* spp.), meadow fescue (*Festuca pratensis*), tall fescue (*Festuca arundinacea*), cereal rye (*Secale cereal*) Russian wild rye (*Psathyrostachys juncea*), oats (*Avena sativa*), bermudagrass (*Cynodon dactylon*), Kentucky bluegrass (*Poa pratensis*), big bluestem (*Andropogon gerardii*), little bluestem (*Schizachyrium scoparium*), blue grama (*Bouteloua gracilis*), black grama (*Bouteloua eriopoda*), side-oat grama (*Bouteloua curipendula*), johnsongrass (*Sorghum halepense*), buffalograss (*Buchloe dactyloides*), and creeping bentgrass (*Agrostis stolonifera*). In some aspects, the host plant is defined as a monocot. In certain aspects, the host plant is a monocot that produces food. In certain aspects, the host plant is a monocot that produces feed or grazing material for livestock. In one embodiment, the host plant is a grass host plant such as switchgrass (*Panicum virgatum*). In some embodiments, the host plant is not switchgrass.

The *S. bescii* endophyte of the present disclosure may be introduced or maintained in dicots. By way of example but not limitation, such dicots include alfalfa (*Medicago sativa*), rose (*Rosa* spp.), tomato (*Solanum lycopersicum*), blueberry (*Vaccinium* spp.), cotton (*Gossypium hirsutum*), pepper (*Capsicum* spp.), common bean (*Phaseolus vulgaris*), lentil (*Lens culinaris*), peas (*Pisum sativum*), eggplant (*Solanum melongena*), watermelon (*Citrullus lanatus*), coffee (*Coffea* spp.), apples (*Malus domestica*), plums (*Prunus domestica*), sweet cherry (*Prunus avium*), squash (*Cucurbita pepo* L.), broccoli (*Brassica oleracea*), turnips (*Brassica rapa*), geraniums (*Geranium* spp.), strawberry (*Fragaria*x *ananassa*), soybean (*Glycine max*), and pecan (*Carya illinoinensis*). In an embodiment, the host plant is pecan. In some embodiments, the pecan is chosen from the Kanza, Peruque and Giles cultivars. In an embodiment, the host plant is defined as a dicot. In some embodiments, the host plant is an ornamental. In some embodiments, the host plant is a dicot crop that produces human good. In certain aspects, the host plant is a dicot crop that produces feed or grazing material for livestock. In an embodiment, the host plant is alfalfa (*Medicago sativa*).

It should be understood that, in some embodiments, the *S. bescii* endophyte of the present disclosure comprises the nucleotide sequence of SEQ ID NO: 1, which also includes the nucleotide sequence of SEQ ID NO: 2. In some embodiments, the *S. bescii* endophyte comprises the nucleotide sequence of SEQ ID NO: 2. However, this disclosure is intended to include the *S. bescii* endophyte as modified, where modification(s) to the sequence of SEQ ID NO: 1 or SEQ ID NO: 2 are made artificially. Thus, *S. bescii* strains derived from a *S. bescii* endophyte having the nucleotide sequence of SEQ ID NO: 2 or SEQ ID NO: 1 are within the contemplated scope of the present disclosure.

The following examples are included to demonstrate preferred embodiments of the present disclosure. Those of skill in the art should, in light of the present disclosure, appreciate that many changes can be made in the specific embodiments which are disclosed and still obtain a like or similar result without departing from the concept, spirit and scope of the present disclosure.

EXAMPLES

Example 1

Isolation and Characterization of *Serendipita bescii* from Switchgrass Root Samples 63 root samples were collected from switchgrass plants collected from Noble Research Institute's switchgrass field located in Ardmore, Okla., United States (coordinates 34.193389, −97.086004). The switchgrass plants were originally collected from the Tallgrass Prairie Preserve (TGPP) located in Northern Oklahoma and planted in the Noble Foundation Research Institute's switchgrass plot in Oklahoma. The switchgrass plant denoted as C2 (also known as 7W in the Noble Research Institute's switchgrass field), from which *S. bescii* was isolated as described below, was originally located at coordinates 36.8102, 97.527 and the switchgrass plant denoted as C4 (also known as 31E in the Noble Research Institute's switchgrass field) was originally located at coordinates 36.76877, 96.39035. The root samples were thoroughly washed in running water to remove adhered soil particles. Root samples from each plant were treated individually. Cleaned root samples were cut into 1 cm pieces, homogenized and divided into two samples. The first sample was subjected to DNA extraction while the second sample was blot dried and maintained at 4° C. for downstream processing.

The first sample for each root sample was ground in liquid nitrogen in a TissueLyser II (Retsch, Germany). gDNA was extracted from the lyophilized tissue using a QIAGEN MagAttract 96 DNA Plant Core Kit according to the manufacturer's instructions and quantified using a Nanodrop ND-1000 (Wilmington, Del., United States). The 3' region of the 18S (SSU), ITS1 and ITS2, the 5.8S ribosomal subunit and the 25-28S (LSU) of Serendipitaceae were amplified by direct PCR using the primers NS23 (SEQ ID NO: 3) and NLSeb2R (SEQ ID NO: 4). Each 25 μl PCR reaction included 12.5 μl GO TAQ GREEN MASTER MIX®, 1.25 μl of each primer (0.5 μM) and 10 ng of total genomic DNA. Negative controls containing all reagents except the genomic DNA template were used in all PCR arrays.

Thermocycling was performed using initial heating at 94° C. for 2 minutes, followed by 30 cycles of denaturation at 94° C. for 45 seconds, annealing at 60° C. for 45 seconds and extension at 72° C. for 2.5 minutes. The final extension was performed at 72° C. for 10 minutes. The presence and yield of PCR products were monitored by agarose gel electrophoresis followed by visualization with ethidium bromide staining and UV illumination.

Using direct PCR, it was possible to amplify a ~2.2 kb fragment. PCR of the root samples yielded 36 out of 63 samples with a ~2.2 kb fragment with 27 samples yielding no PCR product. The PCR product was subsequently gel purified using the QIAguick Gel Extraction Kit® and submitted for sequencing using the same set of primers at Noble Research Institute's genomics Core Facility. DNA sequences were manually inspected, edited using geneious version 6.1.2 (Biomatters Auckland, New Zealand). The sequences were then subjected to BLASTn searches against the NCBI nonredundant database (GenBank) for sequence identities with known *Serendipita* sequences. Out of the 36 samples, three sequences were identified as closely related to Serendipitaceae sequences from GenBank. The phylogenetic affinities of these three sequences, designated NFSgF_C2, NFSgF_C4 and NFSgF_C12, with known serendipitoid sequences from GenBank and reference strains from *S. vermifera* isolated from Australian orchid were determined by the UPGMA method as shown in FIG. 1.

To purify and eventually increase the percent colonization or relative abundance of *Serendipita* biomass in planta, the trap culture method was used in the switchgrass (*Panicum virgatum*_L) cultivar Alamo as a host. Surface sterilized root materials, known to have been infected with *Serendipita* on the basis of the foregoing sequence analysis were finely chopped and mixed with steile Metromix-350 medium (Scotts-Sierra Horticultural Products, Marysville, Ohio, United States). D25L single cell root trainers (5 cm diameter and 25 cm height, Stuewe & Sons, Inc., Oregon, United States) were filled with this mixture. Each root trainer was potted with a single in vitro germinated sterile seedling of switchgrass cultivar Alamo. The plants were maintained in a greenhouse for 4-5 months.

Figure 2:
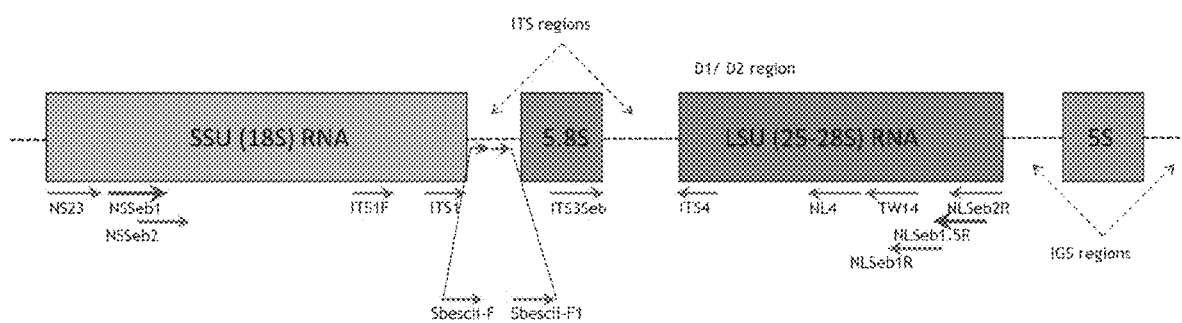
FIG. 2 depicts a map of ribosomal DNA of Serendipitaceae with exemplary primers for amplifying portions thereof by PCR. Exemplary forward primers include NS23 (SEQ ID NO: 3), NSSeb1 (SEQ ID NO: 5), NSSeb2 (SEQ ID NO: 21), ITS1F (SEQ ID NO: 19), ITS1 (SEQ ID NO: 20), Sbescii-F (SEQ ID NO: 17), Sbescii-F1 (SEQ ID NO: 11) and ITS3Seb (SEQ ID NO: 7). Exemplary reverse primers include ITS4 (SEQ ID NO: 12), NL4 (SEQ ID NO: 8), TW14 (SEQ ID NO: 18), NLSeb2R (SEQ ID NO: 4), NLSeb1.5R (SEQ ID NO: 6), and NLSeb1R (SEQ ID NO: 22). Sbescii-F1 (SEQ ID NO: 11) and Sbescii-F (SEQ ID NO: 17) are specific to *S. bescii*.

After 4-5 months of greenhouse culture, colonization of Serendipitaceae was confirmed by nested PCR using sets of *Serendipita* specific primers. A map of the genetic sequence of the ribosomal DNA of *Serendipita* is shown in FIG. 2 aligned with primers that can be used to amplify portions of the ribosomal DNA. gDNA was isolated and quantified by the same method used for the original root samples. The 3' region of the 18S (SSU), ITS1 and ITS2, the 5.8S ribosomal subunit and the 25-28S (LSU) of Serendipitaceae were amplified by direct PCR using the primers NSSeb1 (SEQ ID NO: 5) and NLSeb1.5R (SEQ ID NO: 6). Each 25 µl PCR reaction included 12.5 µl GO TAQ GREEN MASTER MIX®, 1.25 µl of each primer (0.5 µM) and 10 ng of total genomic DNA. A ~2.2 kb fragment was obtained from the direct PCR reaction. This fragment was diluted 1:200 and used as a template for a first nested PCR (nPCR-I) using the primers ITS3Seb (SEQ ID NO: 7) and NL4 (SEQ ID NO: 8) and a second nested PCR (nPCR-II) using S. vermifera (MAFF305830) specific primers ITS3Seb-MS (SEQ ID NO: 10) and ITS3Seb-R (SEQ ID NO: 9) covering the 3' region of the 5.8S, the highly variable ITS2 region and the 5' region of the 25-28S (LSU) of Serendipitaceae rDNA.

Thermocycling for direct PCR was performed using initial heating at 95° C. for 3 minutes, followed by 35 cycles of denaturation at 95° C. for 30 seconds, annealing at 59° C. for 30 seconds and extension at 72° C. for 2 minutes. The final extension was performed at 72° C. for 10 minutes. For nPCR-I, thermocycling consisted of initial heating at 95° C. for 3 minutes, followed by 20 cycles of denaturation at 95° C. for 30 seconds, annealing at 60° C. for 30 seconds and extension at 72° C. for 1 minute. The final extension was performed at 72° C. for 10 minutes. For nPCR-II, thermocycling consisted of initial heating at 95° C. for 3 minutes, followed by 20 cycles of denaturation at 95° C. for 30 seconds, annealing at 62° C. for 30 seconds and extension at 72° C. for 30 seconds. The final extension was performed at 72° C. for 10 minutes. For all PCR reactions, negative controls containing all reagents except the DNA template and positive control containing S. vermifera (MAFF305830) gDNA were used. PCR products were direct sequenced and blasted against the GenBank database for Serendipita vermifera. nPCR-I yielded a ~1 kb fragment which indicated Serendipita colonization and nPCR-II did not yield any further bands which confirmed that the strains were distinct from S. vermifera (MAFF305830).

Figure 3:
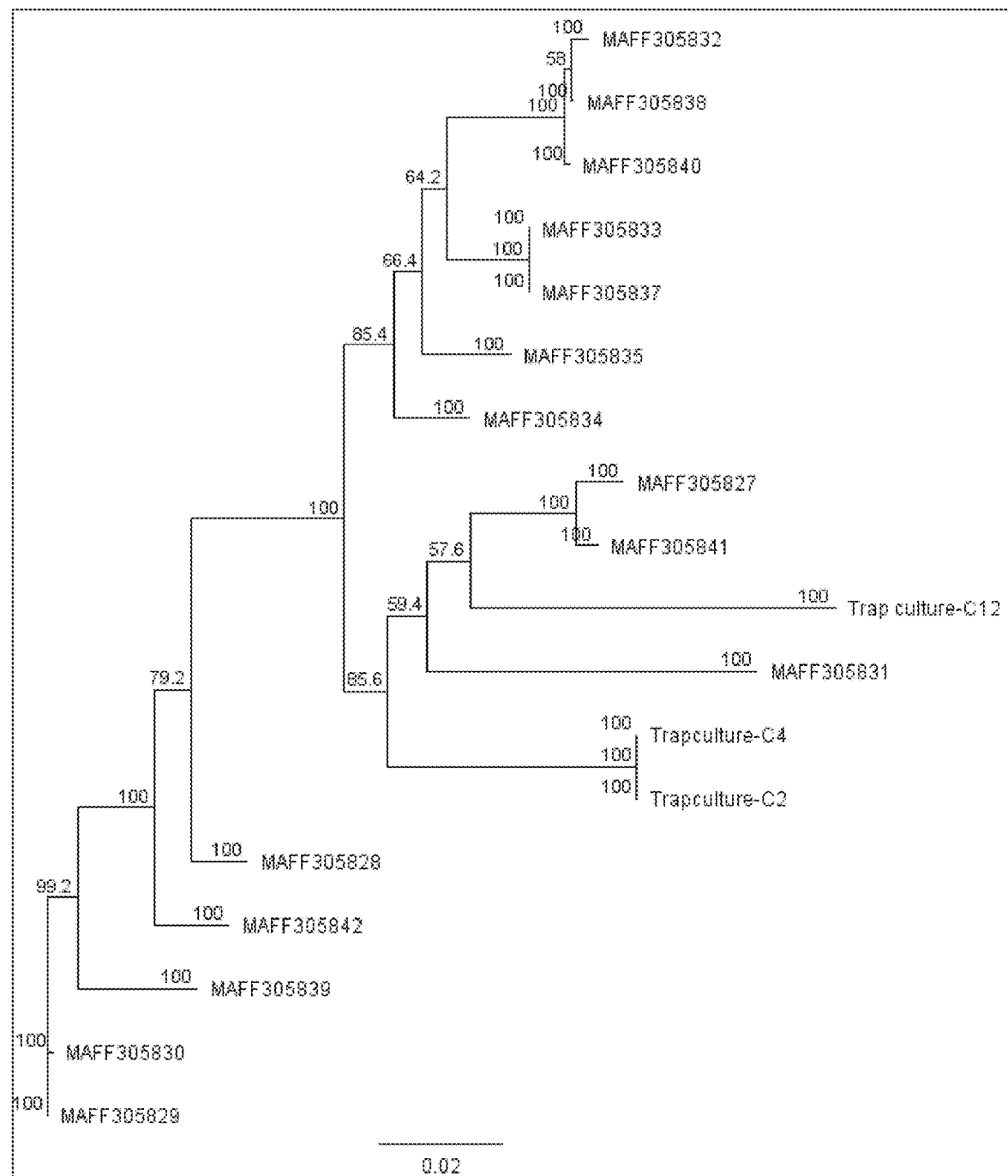
FIG. 3 depicts the phylogenetic relationship between three Serendipitoid sequences detected in switchgrass roots from trap culture with serendipitoid sequences from GenBank and reference strains of *S. vermifera* isolated from Australian orchid reconstructed by the UPGMA method for 20 partial 18S/5.8S/partial LSU rDNA sequences (alignment length 750 bp). Numbers are UPGMA bootstrap values based on 500 replicates. The bar indicates substitutions per site.

The results demonstrated that the sequences are derived from Serendipita vermifera. The sequences were curated for chimeric sequences and multiple sequence alignment and phylogenetic distance was estimated with reference strains of Serendipita vermifera (Australian orchid). The phylogenetic affinities of the three sequences, designated Trapculture-C2 (from the sample yielding NFSgF_C2), Trapculture-C4 (from the sample yielding NFSgF_C4) and Trap culture-C12 (from the sample yielding NFSgF_C12), with known serendipitoid sequences from GenBank and reference strains from S. vermifera isolated from Australian orchid were determined by the UPGMA method as shown in FIG. 3.

Root samples were collected from trap culture from the sample yielding Trapculture-C2 and cleaned by washing with running water. The samples were surface sterilized with 70% ethanol for 5 minutes followed by 2% sodium hypochlorite for 1 minute and washing with sterile water. Samples were then plated onto Modifed Melin Norkan's agar, pH 8 (MMN agar plates) amended with Ampicillin (1000 mg L$^{-1}$), Chloramphenicol (50 mg L$^{-1}$) and Streptomycin (50 mg L$^{-1}$), Benomyl (4 mg L$^{-1}$) and Dichloran (8 mg L$^{-1}$). Plates were incubated in the dark at 24° C. and examined regularly for emerging fungal colonies. Emerging fungal colonies were passed through several rounds of subculture until pure axenic cultures were obtained which were then maintained on MMN agar plates for DNA extraction. A single axenic culture was obtained from Trapculture-C2 which was used for further analysis.

Figure 5:
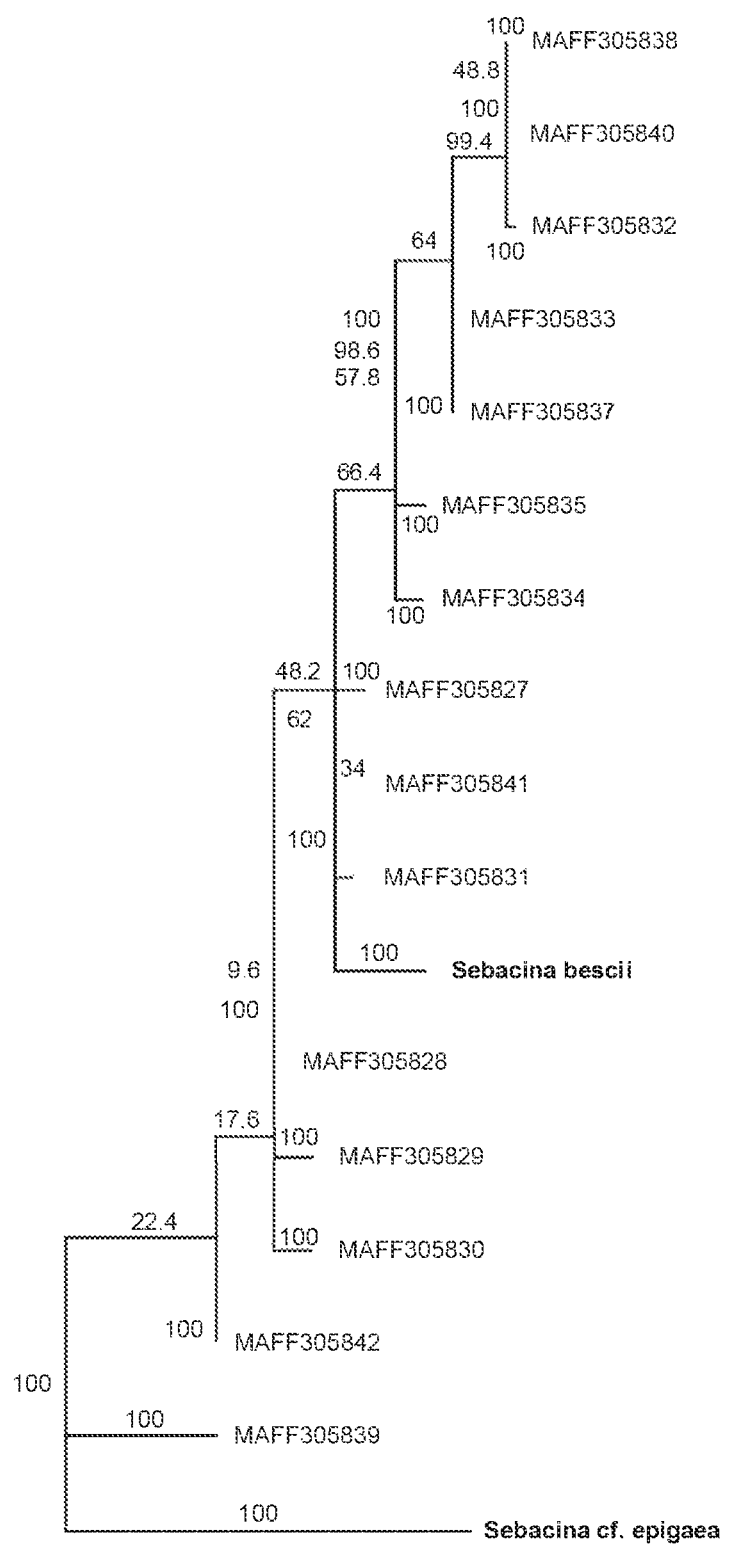
FIG. 5 depicts the phylogenetic relationship between reference strains of *S. vermifera* isolated from Australian Orchid with the new strain of *Serendipita* (*S. bescii*) isolated from switchgrass reconstructed by the UPGMA method for 17 partial 18S/5.8S/partial LSU rDNA sequences (alignment length 630 bp). Numbers are UPGMA bootstrap values based on 500 replicates. The bar indicates substitutions per site.
Figure 6:
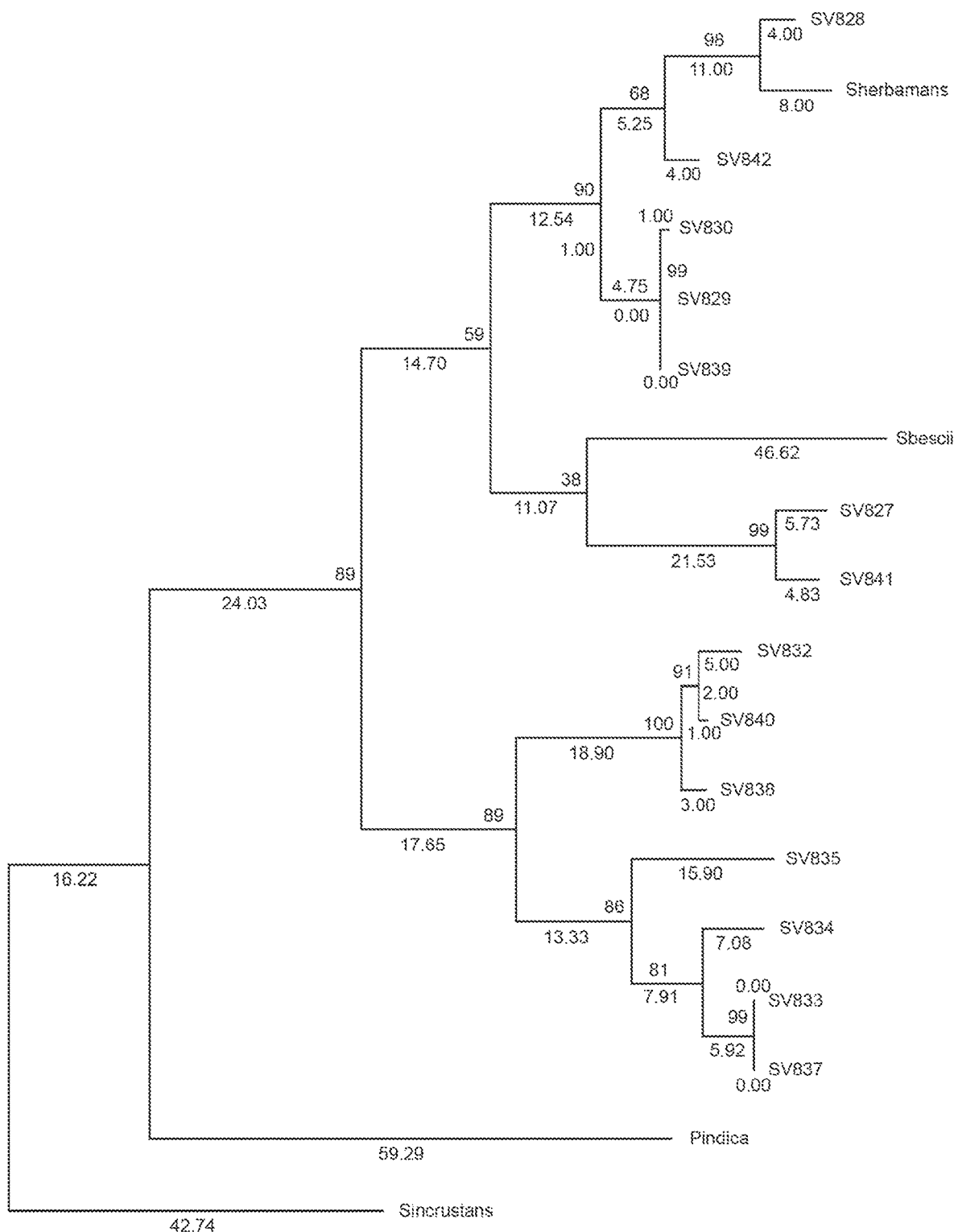
FIG. 6 depicts the phylogenetic relationship of *S. bescii* to *S. vermifera* strains using the Maximum Parsimony method. Tree #1 out of 3 most parsimonious trees (length=395) is shown. The percentage of replicate trees in which the associated taxa clustered together in the bootstrap test (500 replicates) are shown next to the branches. The MP tree was obtained using the Subtree-Pruning-Regrafting (SPR) algorithm. Branch lengths were calculated using the average pathway method and re in the units of the number of changes over the whole sequence. They are shown next to the branches. The tree is drawn to scale. All positions containing gaps and missing data were eliminated. There were a total of 499 positions in the final dataset. Evolutionary analyses were conducted in MEGA6.

DNA extraction and quantification was performed as described previously. Nested PCR based screening was performed using the same method as applied for the assessment of trap culture for Serendipita colonization using NSSeb1 (SEQ ID NO: 5) and NLSeb1.5R (SEQ ID NO: 6) primers for direct PCR, ITS3Seb (SEQ ID NO: 7) and NL4 (SEQ ID NO: 8) primers for one nested PCR (nPCR-I) and S. vermifera (MAFF305830) specific ITS3Seb-MS (SEQ ID NO: 10) and ITS3Seb-R (SEQ ID NO: 9) primers for other nested PCR (nPCR-II). The PCR products were submitted for sequencing with the same set of primers at Noble Foundation's genomics Core Facility. DNA sequences were manually inspected, edited using geneious version 6.1.2 (Biomatters Auckland, New Zealand). The sequences were then subjected to BLASTn searches against the NCBI nonredundant database (GenBank) for sequence identities with known Serendipita sequences. The axenic culture obtained was identified as a new strain, designated Serendipita vermifera ssp. bescii ("S. bescii"). In addition, a trap culture was set up in a rhizobox with two switchgrass plants having a Serendipita sequence of Trapculture-2 on either side of an orchid plant with membranes between the three plants. Invasion of the switchgrass roots into the orchid portion of the rhizobox was observed and samples of these roots were collected and DNA analysis performed as above. The sequence alignment of the D1/D2 rDNA sequences of the serendipitoid sequences detected in switchgrass roots from the field, trap culture and from the switchgrass roots in the rhizobox are compared with that from the Serendipita axenic culture, designated Serendipita bescii, are shown in FIG. 4. Phylogenetic maps relating the new strain to known S. vermifera strains are shown in FIGS. 5-6.

Figure 7A:
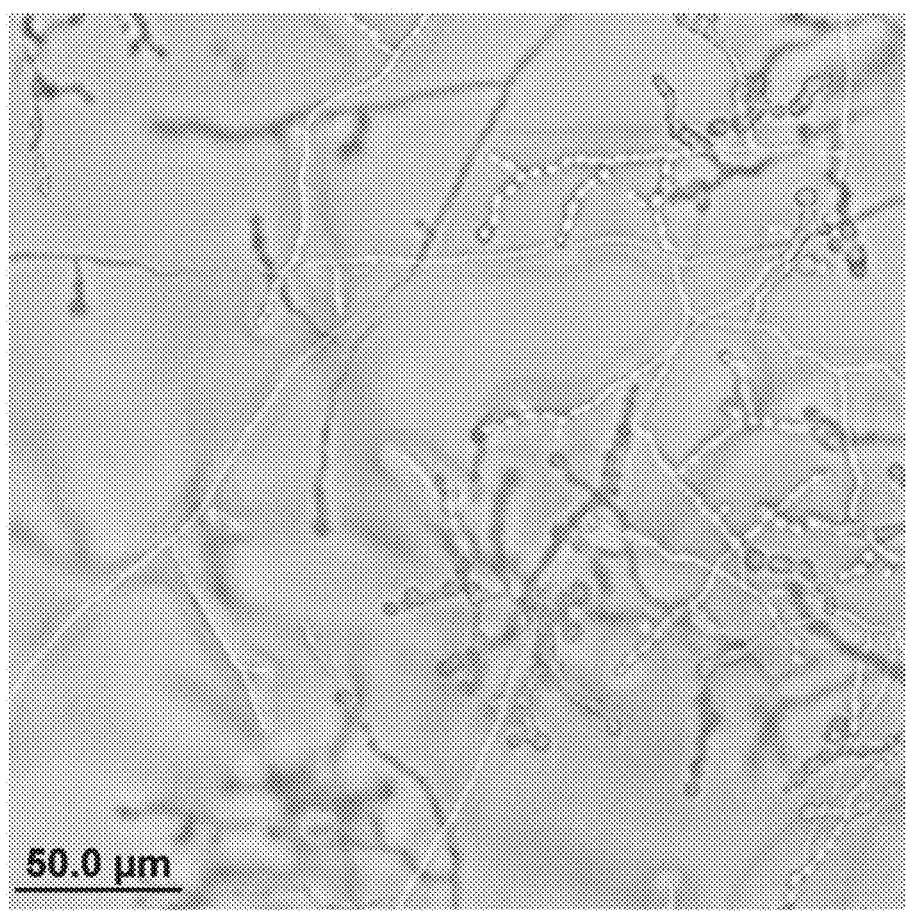
FIG. 7A shows a micrograph of the axenic culture of *S. bescii* using a light microscope. Scale bar=50.0 μm.
Figure 7B:
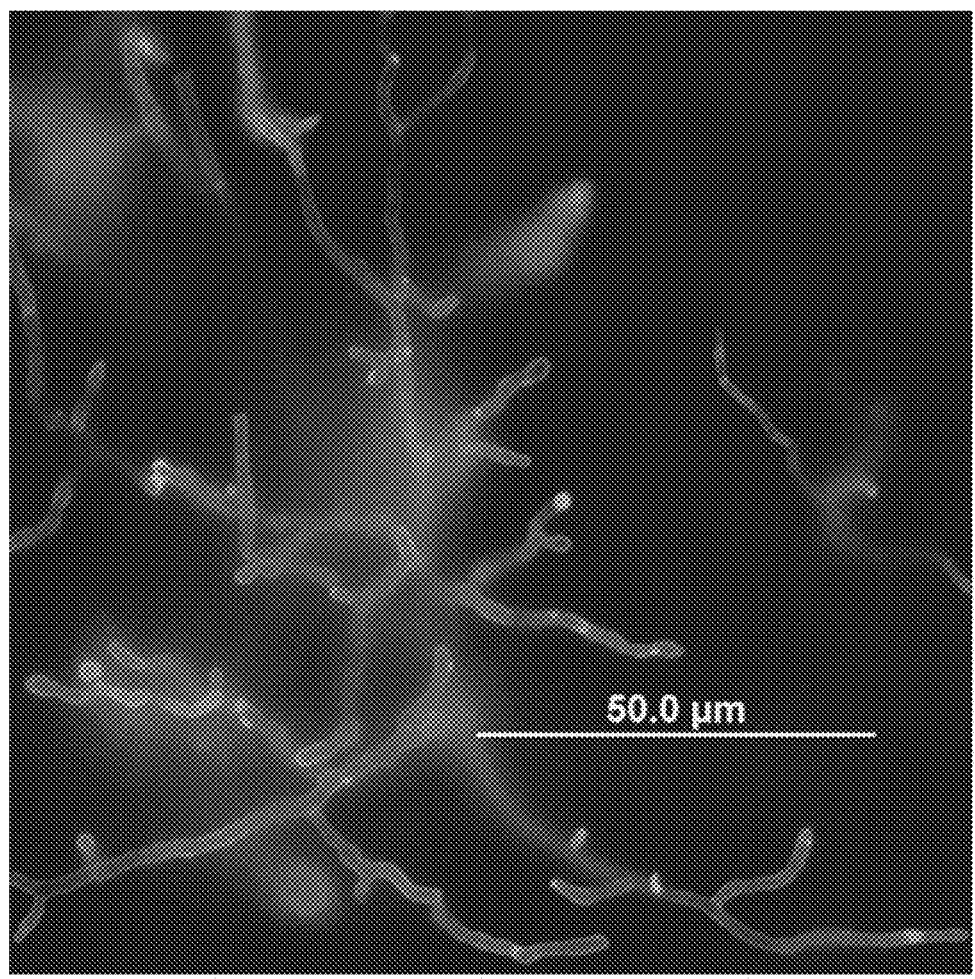
FIG. 7B shows a fluorescent micrograph of the axenic culture of *S. bescii*. Scale bar=50.0 μm.
Figure 7C:
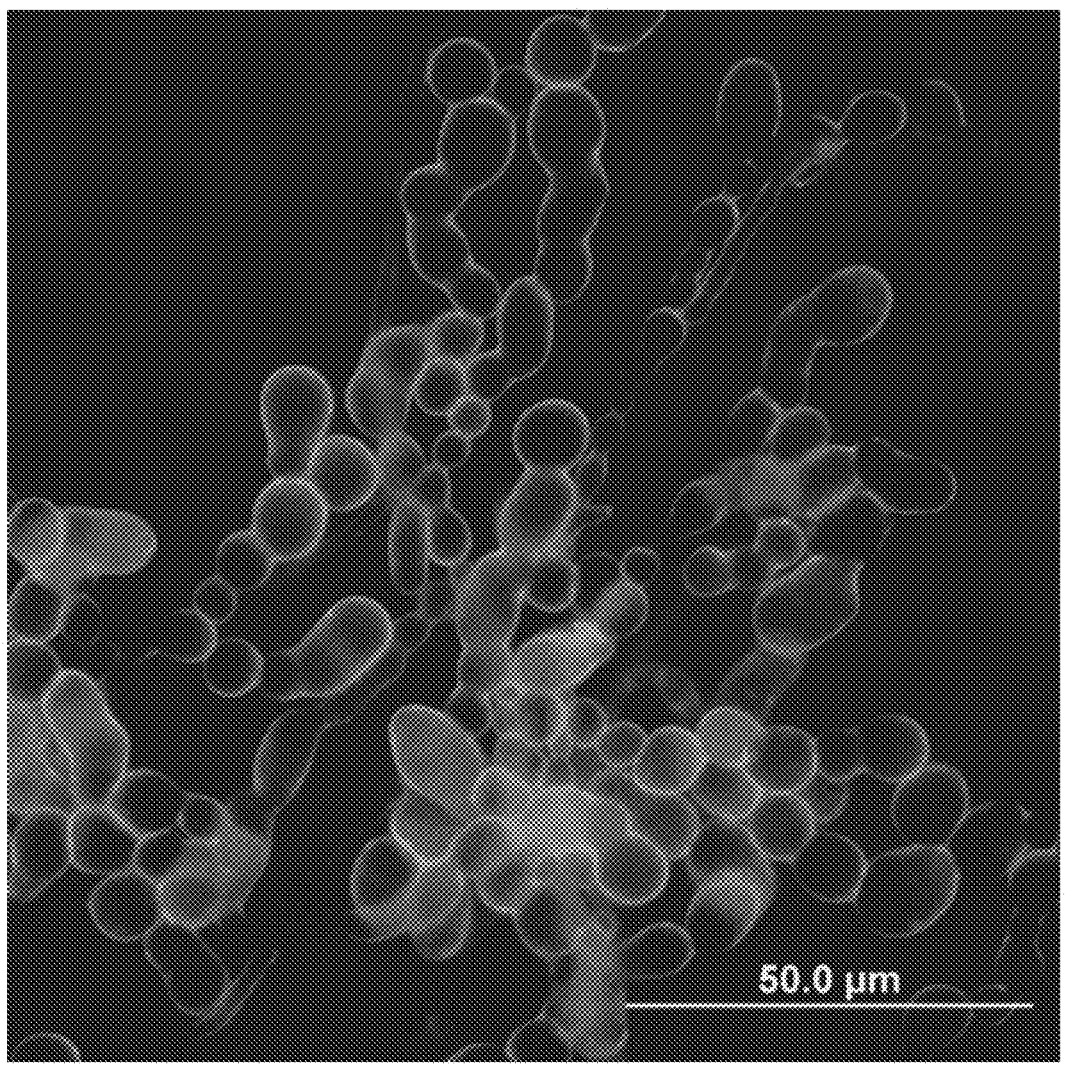
FIG. 7C shows a fluorescent micrograph of the axenic culture of *S. bescii*. Scale bar=50.0 μm.
Figure 7D:
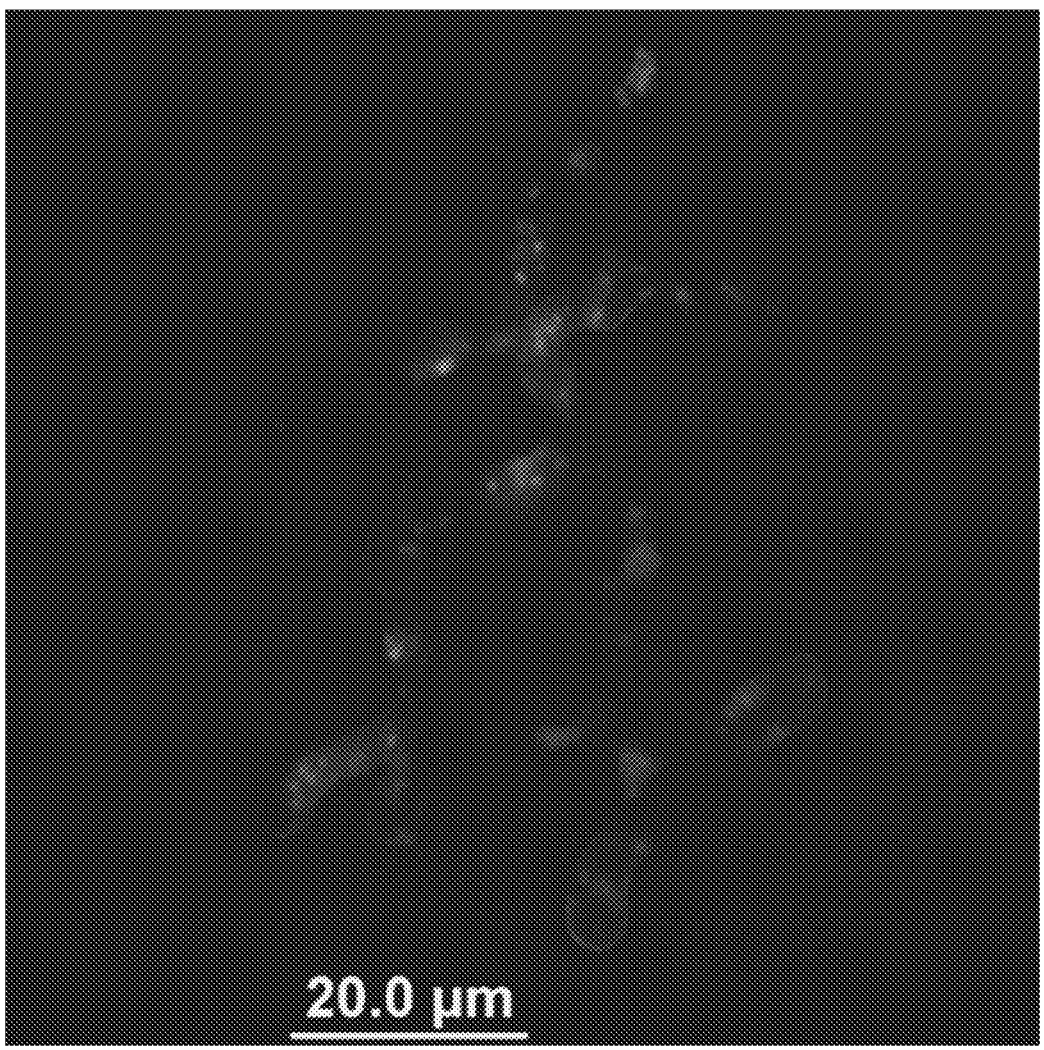
FIG. 7D shows a fluorescent micrograph of the axenic culture of *S. bescii* after DAPI staining. Scale bar=20.0 μm.
Figure 8A:
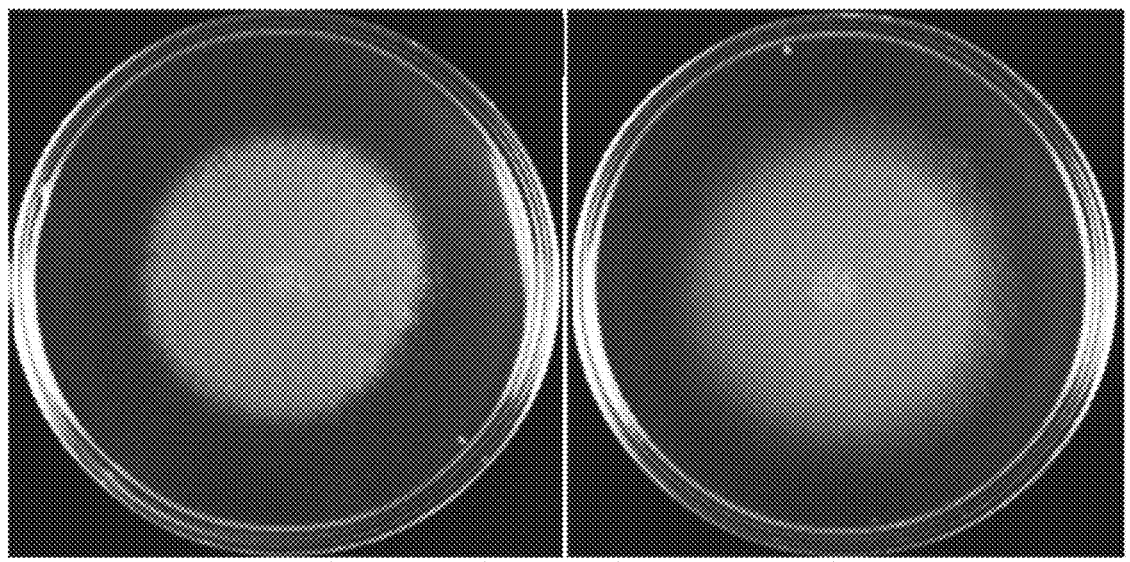
FIG. 8A shows micrographs colonies of the axenic cultures of *S. bescii* and *S. vermifera* (MAFF305830) on MMN agar. Scale bar=50.0 μm.

The axenic culture of the new isolate was viewed under a light microscope and imaged as shown in FIG. 7A. The axenic culture of the new isolate and an axenic culture of S. vermifera (MAFF305830), obtained by the trap culture methods discussed above, were also stained in a 10 µg/ml solution of WGA-AF® 488 (Life Technologies, Carlsbad, Calif., United States) in 1×PBS and visualized under an Olympus fluorescent compound microscope (Nikon, United States) as shown in FIGS. 7B-7D (S. bescii only) which show normal hyphae, monilioid hyphae and DAPI staining, respectively. FIGS. 8A-8B show light and fluorescent micrographs for comparison of the axenic cultures of S. bescii and S. vermifera (MAFF305830) stained using WGA-AF® 488. Similar staining and imaging was performed on switchgrass roots colonized with S. bescii or S. vermifera (MAFF305830) as shown in FIG. 8C.

Figure 9:
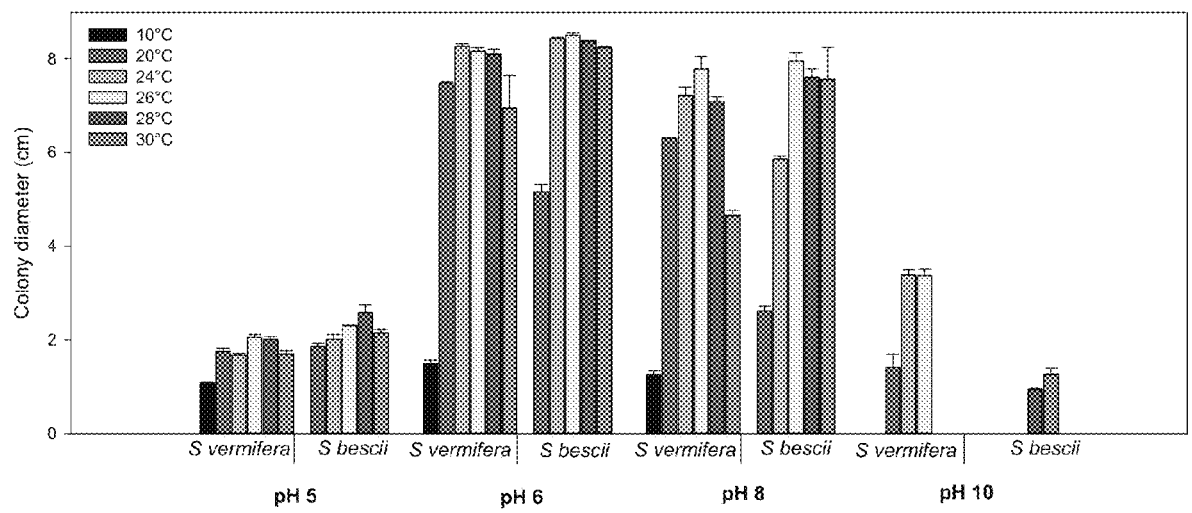
FIG. 9 depicts the colony diameter (cm) 14 days post-inoculation for axenic cultures of *S. vermifera* (MAFF305830) and *S. bescii* at various temperature and pH conditions on MMN agar. Each data point is the mean of three replicates with standard error of mean.

Growth, as measured by colony diameter 14 days after inoculation, of the S. vermifera (MAFF305830) and S. bescii isolates on MMN agar with varying temperature and pH was also assessed as shown in FIG. 9.

Samples of the axenic culture of the new isolate, designated S. bescii, have been deposited with the American Type Culture Collection (ATCC) under designation number PTA-124559 and Strain NFPB0129 by The Noble Research Institute with the ATCC at 10801 University Blvd., Manassas, Va. 20110 United States of America on Nov. 10, 2017 in conformance with the Budapest Treaty on the International Recognition of the Deposit of Microorganisms for the Purposes of Patent Procedure.

Example 2

Growth Promotion Studies Under Normal Watering Conditions

Figure 10:
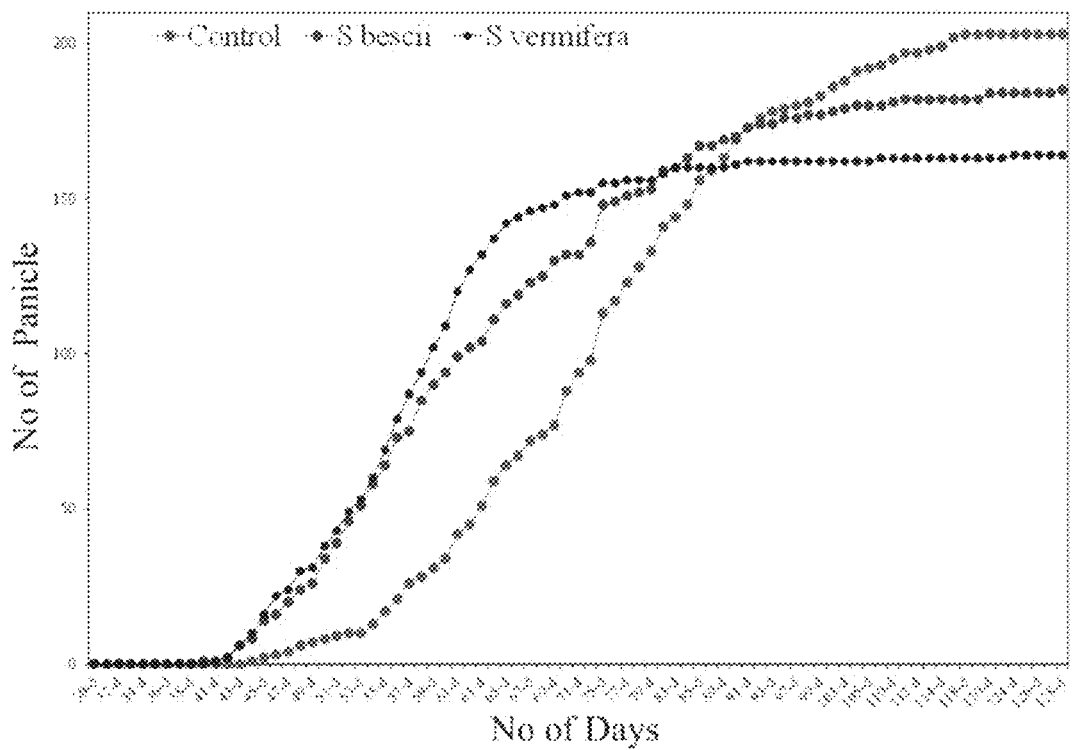
FIG. 10 depicts the grain yield in winter wheat inoculated with *S. bescii*, *S. vermifera* (MAFF305830) or un-inoculated over time. Each data point indicates the total number of panicles produced over time in eight replicate plants for each treatment.

A greenhouse trial was conducted to see the effect of S. bescii on grain yield of winter wheat (OK08328). Plants were colonized in vitro with *S. vermifera* (MAFF305830) and *S. bescii*, respectively. After two weeks, seedlings were vernalized for an additional six weeks before transplanting in Metromix and moving into a greenhouse. An un-inoculated set was maintained under the same conditions throughout for direct comparison. The experimental design consisted of a complete randomized block design with eight replicates per treatment. At maturity, plants were harvested and grain yield data was recorded as shown in Table 1 below and FIG. 10.

TABLE 1

Grain yield data for winter wheat treated with *S. vermifera* (MAFF305830) and *S. bescii* (Different letters indicate a significant difference between treatments at p ≤ 0.05; * = statistically significant)

|  | No. of Panicles | No. of Seeds | Seed weight (g) |
| --- | --- | --- | --- |
| Control | 25.38 +/− 0.91 a | 984.37 +/− 37.07 a | 33.90 +/− 1.31 a |
| *S. bescii* | 23.13 +/− 1.42 ab | 1026.00 +/− 37.21 a | 35.30 +/− 0.86 a |
| *S. vermifera* (MAFF305830) | 20.5 +/− 0.78 b | 960.75 +/− 30.57 a | 35.49 +/− 0.97 a |
| Statistical Significance | * | not significant | not significant |

Example 3

Growth Promotion Studies Under Normal and Restricted Watering Conditions in Winter Wheat

Figure 11B:
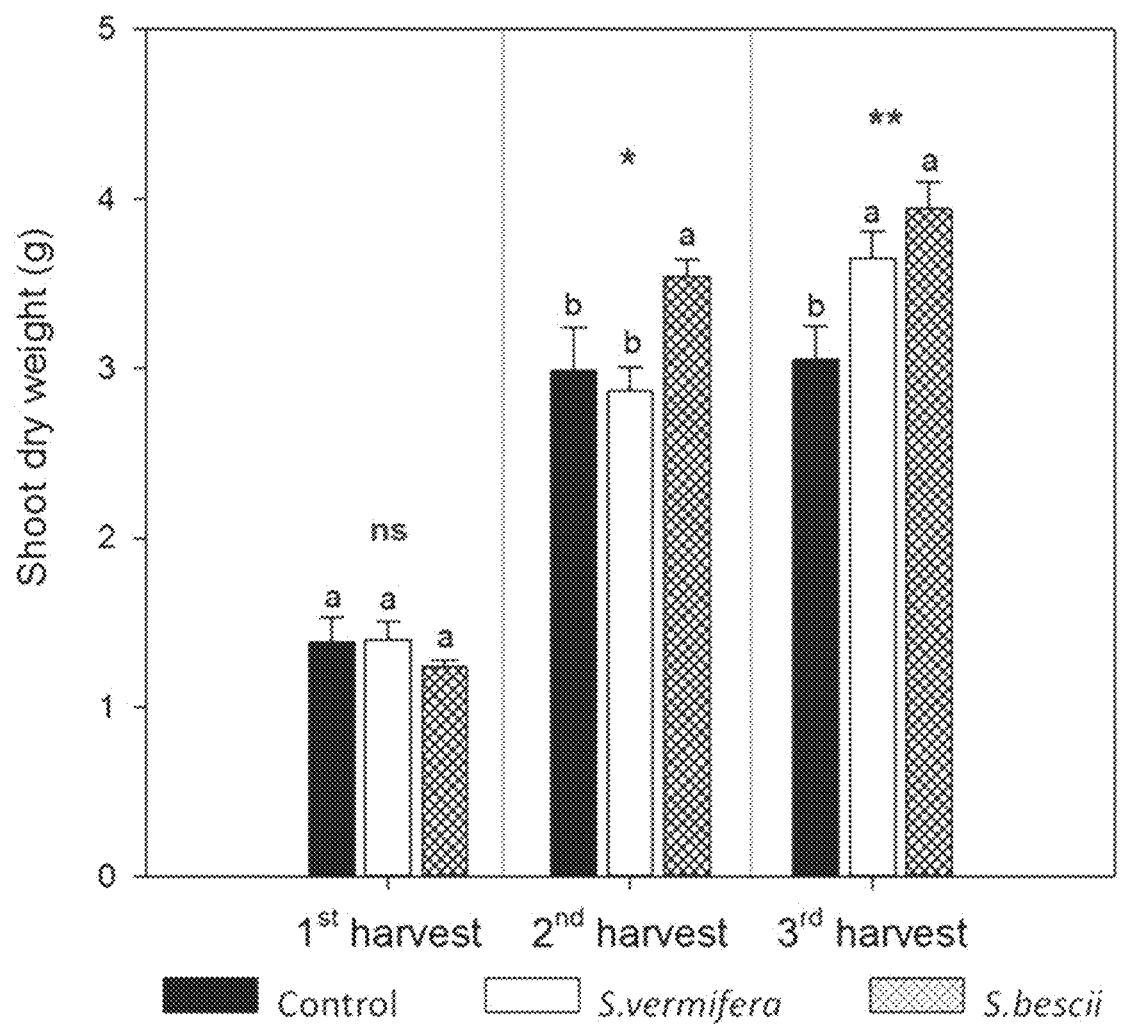
FIG. 11B depicts the forage dry weight under drought conditions for winter wheat inoculated with *S. bescii*, *S. vermifera* (MAFF305830) or un-inoculated over three harvests. Bars with different letters indicate a significant difference between treatment at $p \leq 0.05$.

*Triticum aestivum* (winter wheat—NF 101) was colonized in vitro with *S. vermifera* and *S. bescii* respectively. After 14 days post-inoculation, plants were transplanted in Metromix and maintained in a controlled greenhouse environment. Water restriction was set in effect two weeks after transplantation. The experimental design consisted of three treatments (*S. bescii*, *S. vermifera* and a control (un-inoculated) group) each within normal watering and restricted watering with ten replicates per treatment. Plants were arranged in a randomized complete block design. The data were analyzed using analysis of variance (ANOVA) method. Plants were harvested for forage biomass three times (i.e., once every four weeks). Subsequently, the dried forage were processed for forage quality analysis. An un-inouclated set was maintained under the same conditions throughout for direct comparison. The results of the study are shown in FIGS. 11A-11B which show the shoot dry weight for each treatment at the first, second and third harvests under normal watering (FIG. 11A) and drought (FIG. 11B) conditions.

Example 4

Growth Promotion Studies Under Normal and Restricted Watering Conditions in Alfalfa

Figure 12A:
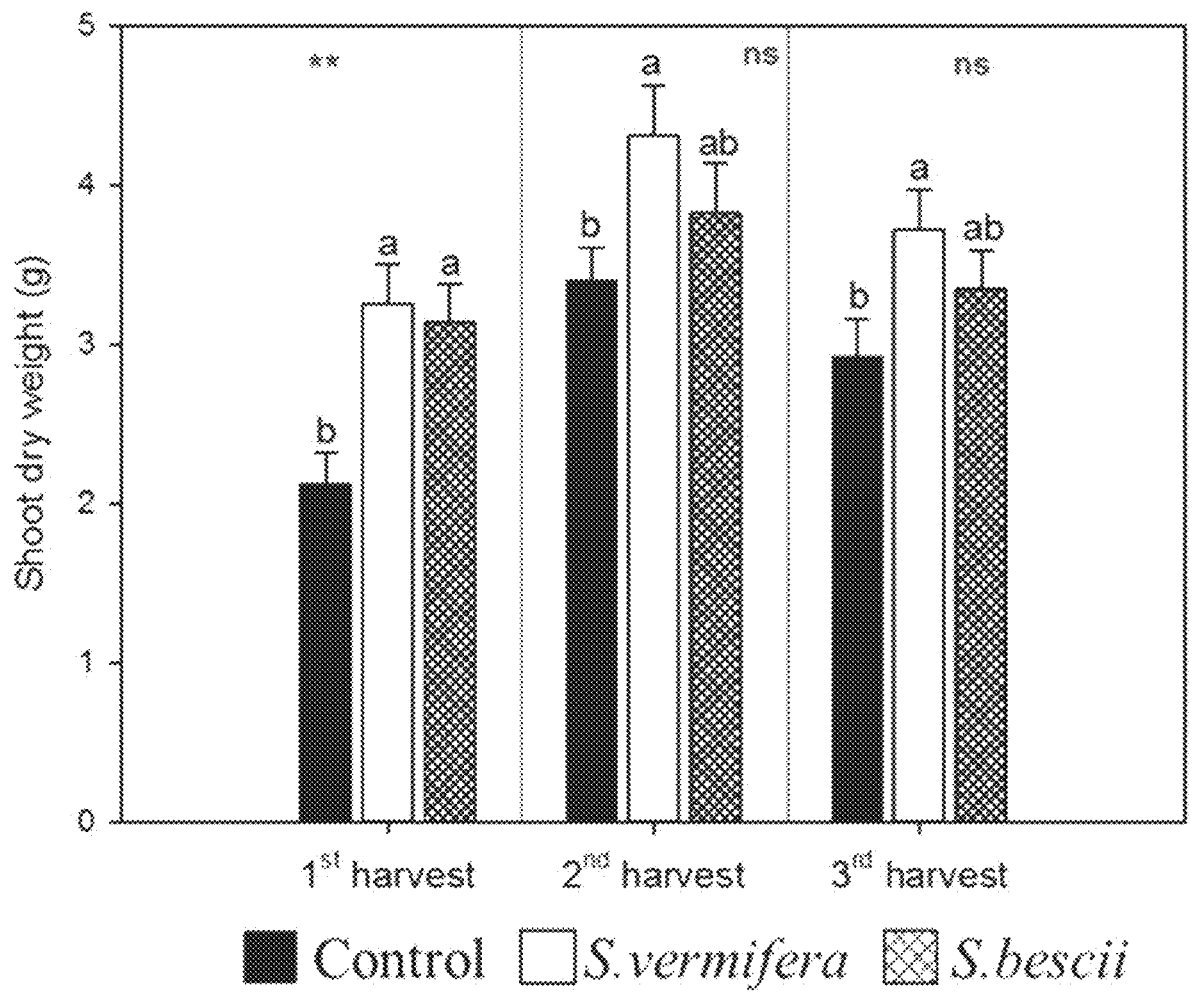
FIG. 12A depicts the forage dry weight under normal watering conditions for alfalfa inoculated with *S. bescii*, *S. vermifera* (MAFF305830) or un-inoculated over three harvests. Bars with different letters indicate a significant different between treatment at $p \leq 0.05$.
Figure 12B:
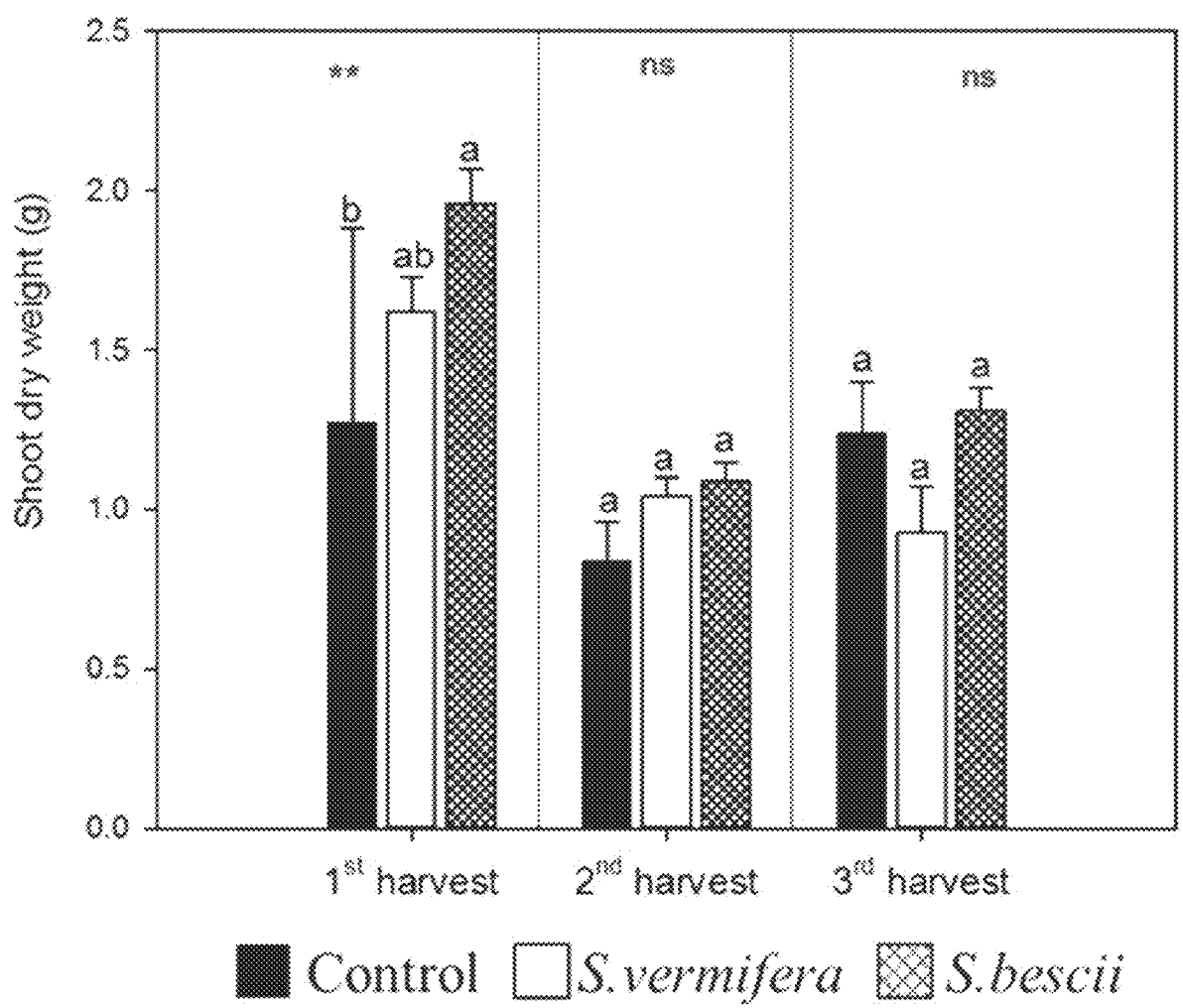
FIG. 12B depicts the forage dry weight under drought conditions for alfalfa inoculated with *S. bescii, S. vermifera* (MAFF305830) or un-inoculated over three harvests. Bars with different letters indicate a significant different between treatment at $p \leq 0.05$.

*Medicago sativa* (NECS-141) cuttings were colonized in vitro with *S. vermifera* and *S. bescii* respectively. After 14 days post-inoculation, plants were transplanted in Metromix and maintained in a controlled greenhouse environment. Water restriction was set in effect two weeks after transplantation. The experimental design consisted of three treatments (*S. bescii*, *S. vermifera* and a control (un-inoculated) group) each within normal watering and restricted watering with ten replicates per treatment. Plants were arranged in a randomized complete block design. The data were analyzed using analysis of variance (ANOVA) method. Plants were harvested three weeks after initiation of water limitation and estimated for forage biomass. Subsequently, the dried forage were processed for forage quality analysis. Samples for the second and third harvests were collected at 60 days and 90 days post-inoculation. An un-inoculated set was maintained under the same conditions throughout for direct comparison. The results of the study are shown in FIGS. 12A-12B which show the shoot dry weight for each treatment at the first, second and third harvests under normal watering (FIG. 12A) and drought (FIG. 12B) conditions.

Example 5

Colonization of Blueberry Plants by *S. bescii*

Blueberries are perennial flowering plants within the genus *Vaccinium* which also includes cranberries, bilberries and grouseberries. Colonization of blueberry roots is generally difficult and positive outcomes are not typical because blueberries, as members of the heath family, Ericaceae, must have symbiotic fungi to live properly, being so adapted to have mycorrhizae as to not have root hairs. Generally, plants of the family Ericaceae, and specifically blueberries, have a type of mycorrhizial association called ericoid mycorrhizae.

Blueberry seedlings were colonized using a bentonite clay-based inoculation method as described in Example 8 below. Plants were maintained in the greenhouse. Roots were collected one month post-colonization. Root samples were analyzed by fluorescent microscopy after staining with WGA-AF® 488 and by PCR using *S. bescii* specific primers (SEQ ID NOs: 11 and 12) and subsequent sequencing.

Figure 13A:
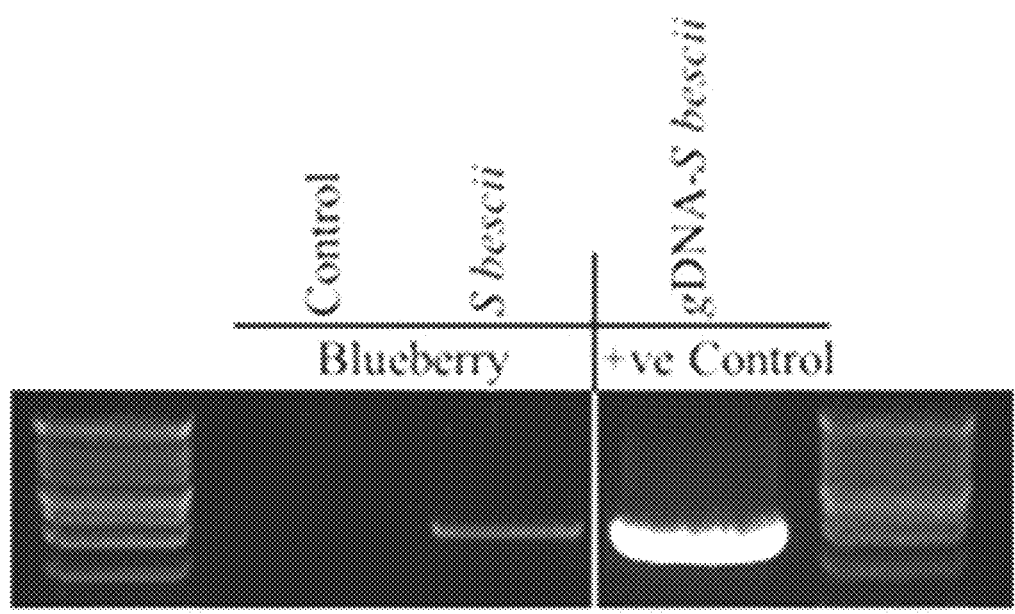
FIG. 13A shows an agarose gel electrophoresis of the PCR product of a blueberry root extract after inoculation with *S. bescii* and a positive control sample of *S. bescii*.
Figure 13B:
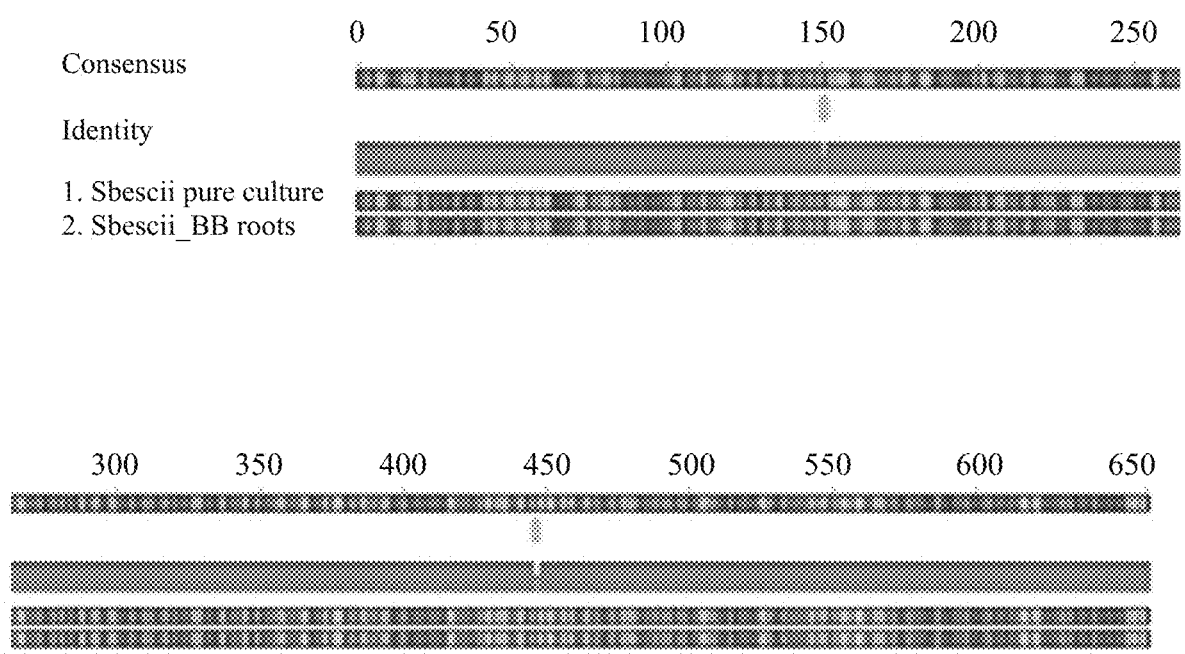
FIG. 13B shows the alignment of PCR sequencing results for a blueberry plant after inoculation with *S. bescii* compared with a pure culture of *S. bescii*.

As shown in FIG. 13A, blueberry roots were effectively colonized by *S. bescii* using a bentonite clay-based inoculation method in sterile Metromix. FIG. 13B shows confirmation of the colonization by sequencing.

Example 6

Effect of *S. bescii* Colonization on Switchgrass Height

Figure 14:
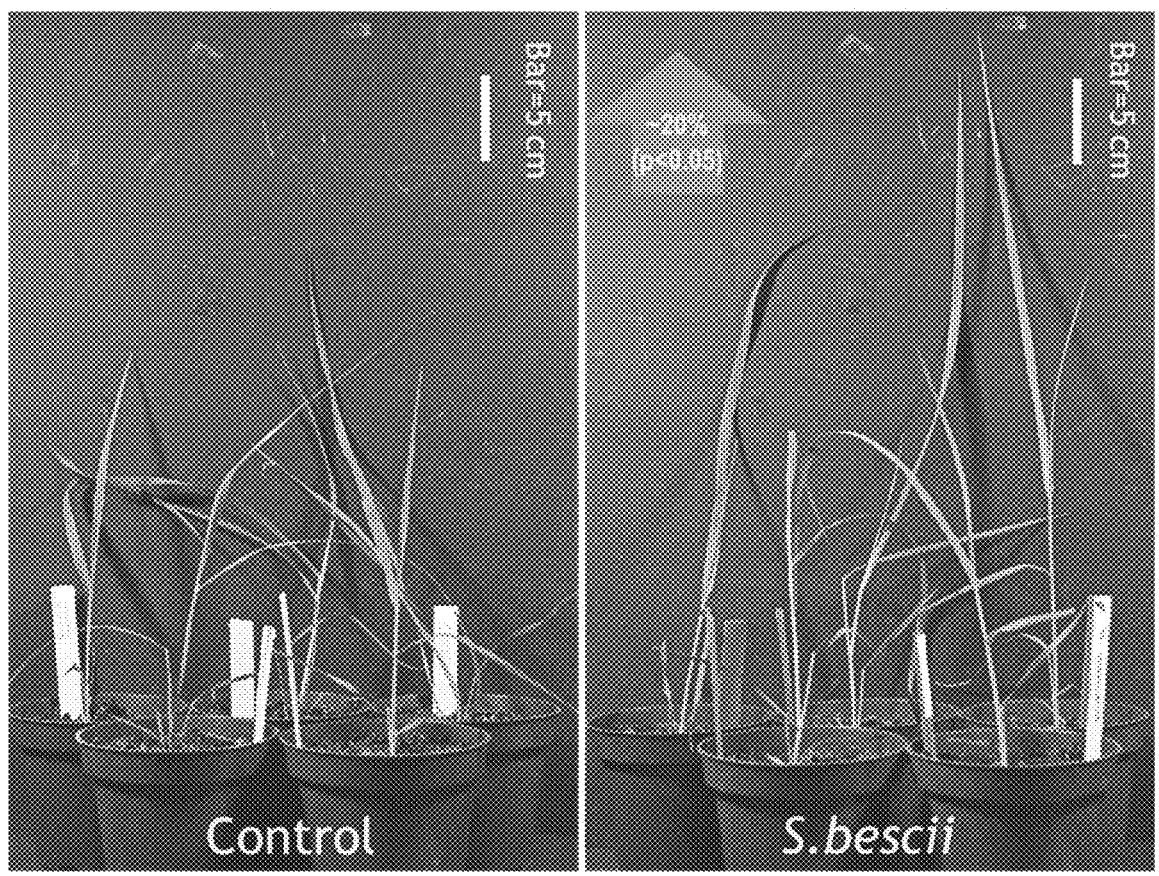
FIG. 14 depicts five replicate plants of a control group of switchgrass plants grown for 4 weeks in a greenhouse and five replicate plants colonized with *S. bescii* grown under the same greenhouse conditions. Scale bar=5 cm.
Figure 15A:
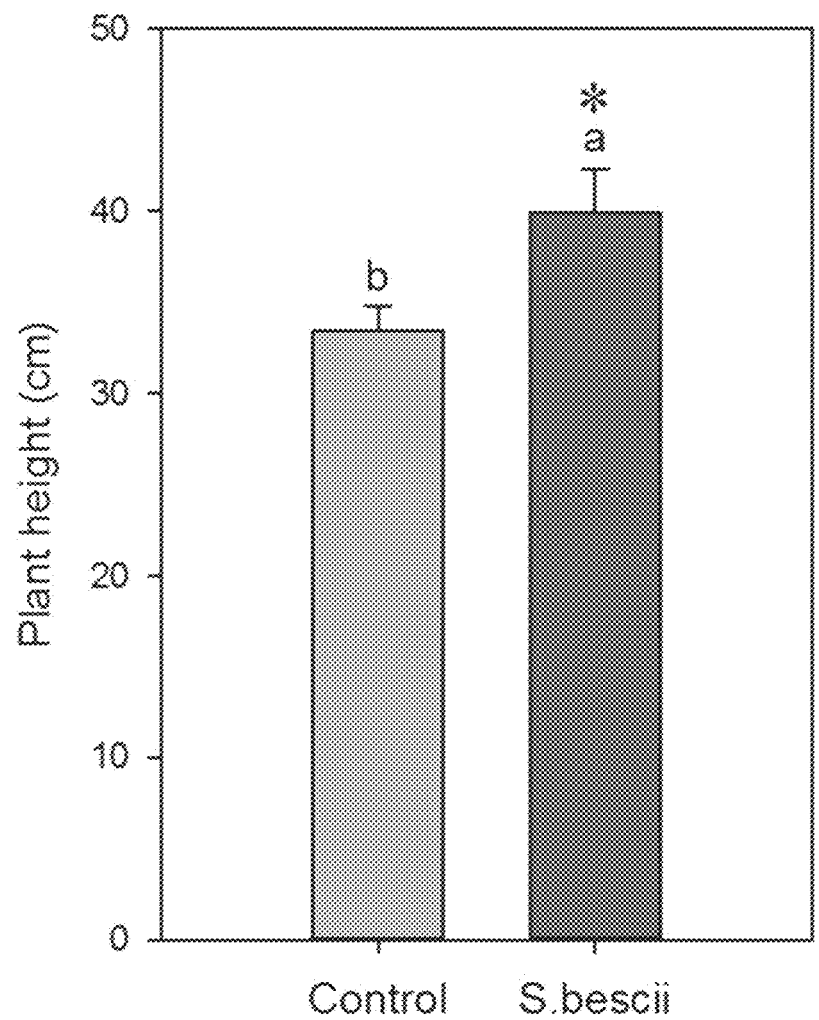
FIG. 15A shows the effect of *S. bescii* colonization on plant height in switchgrass as compared to an un-inoculated control group. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 15B:
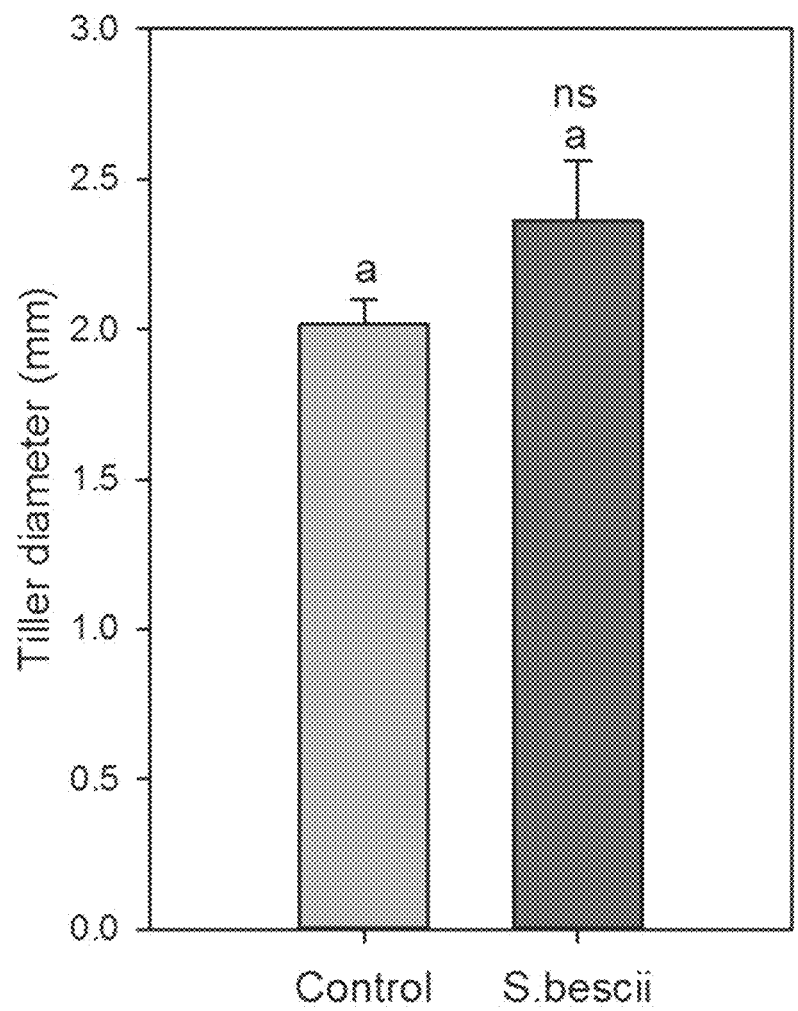
FIG. 15B shows the effect of *S. bescii* colonization on tiller diameter in switchgrass as compared to an un-inoculated control group. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).

Switchgrass (*Panicum virgatum* L) seedlings were colonized in vitro in minimal (M) media with *S. bescii*. Colonization was performed using 175-ml plant containers (5 cm in diameter by 11 cm in height) with lids. The containers were filled with 50 ml of M (minimal) medium pH 5.5 containing 0.3% phytagel amended with 1% sucrose. Clonally propogated switchgrass plants were grown in this medium. For the purpose of in vitro colonization, a seed culture of *S. bescii* was prepared by grinding the mycelia in liquid M media. Individual plants were inoculated with 20 μl of liquid culture by injecting it into the media with a sterile pipette. To maintain uniformity, the media containing the control plants were injected with the same volume of liquid M media. Plants were maintained in a growth chamber at 26° C. under a 17:9 h photoperiod for 2 weeks. After 2 weeks, seedlings were transplanted in ½ gallon pots containing autoclaved Metromix as potting mix. Plants were maintained in the greenhouse for 4 weeks before collecting tiller height and tiller diameter data. The experiment was conducted in five replicates. Un-inoculated plants were maintained in the same way and were used as a control for data analysis. Photographs of five replicate plants for each treatment were taken and are shown in FIG. 14. Data were analyzed using the ANOVA method. When a significant F-test was observed, treatment means were compared using lest significant differences (LSD) at p<0.05 using Costat statistical software 6.4 (Cohort, Berkeley, Calif., United States). The results were plotted graphically using SigmaPlot 12.5 (Systat Software, San Jose, Calif., United States) as shown in FIGS. 15A-15B. As shown, *S. bescii* colonization significantly enhances height (~20%; p<0.05) of switchgrass compared to the control.

Example 7

Figure 16A:
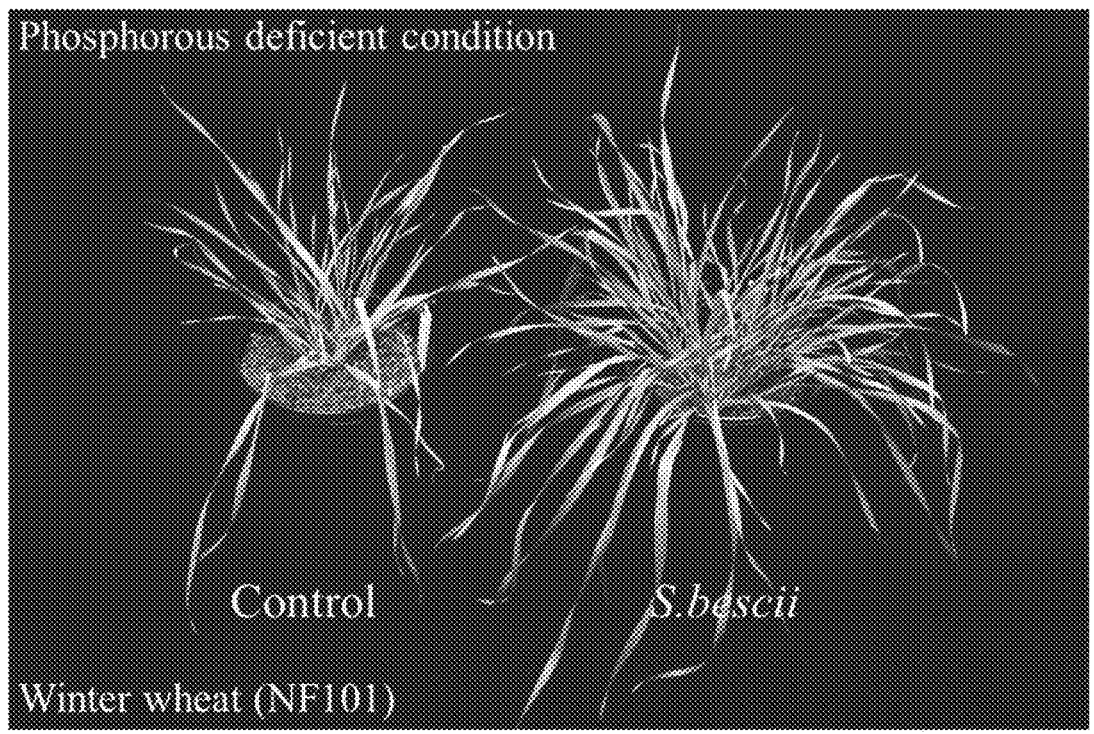
FIG. 16A shows a photograph of representative winter wheat plants grown under phosphorous-deficient conditions with *S. bescii* colonization and without (control).
Figure 16B:
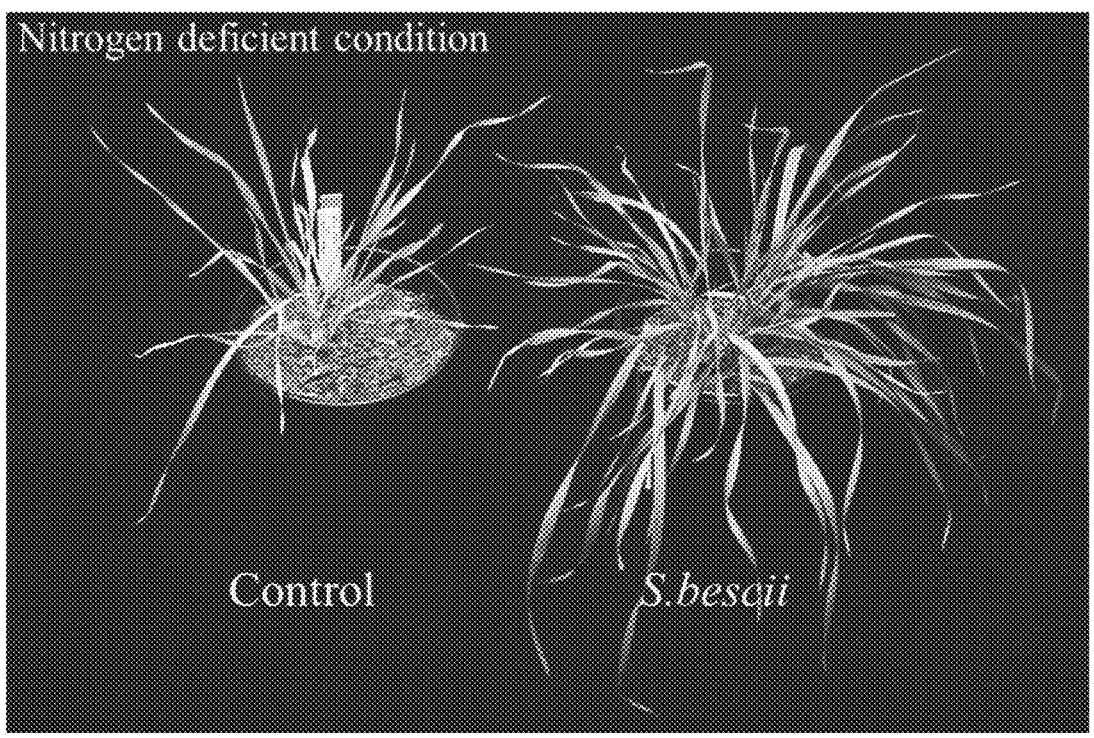
FIG. 16B shows a photograph of representative winter wheat plants grown under nitrogen-deficient conditions with *S. bescii* colonization and without (control).
Figure 17A:
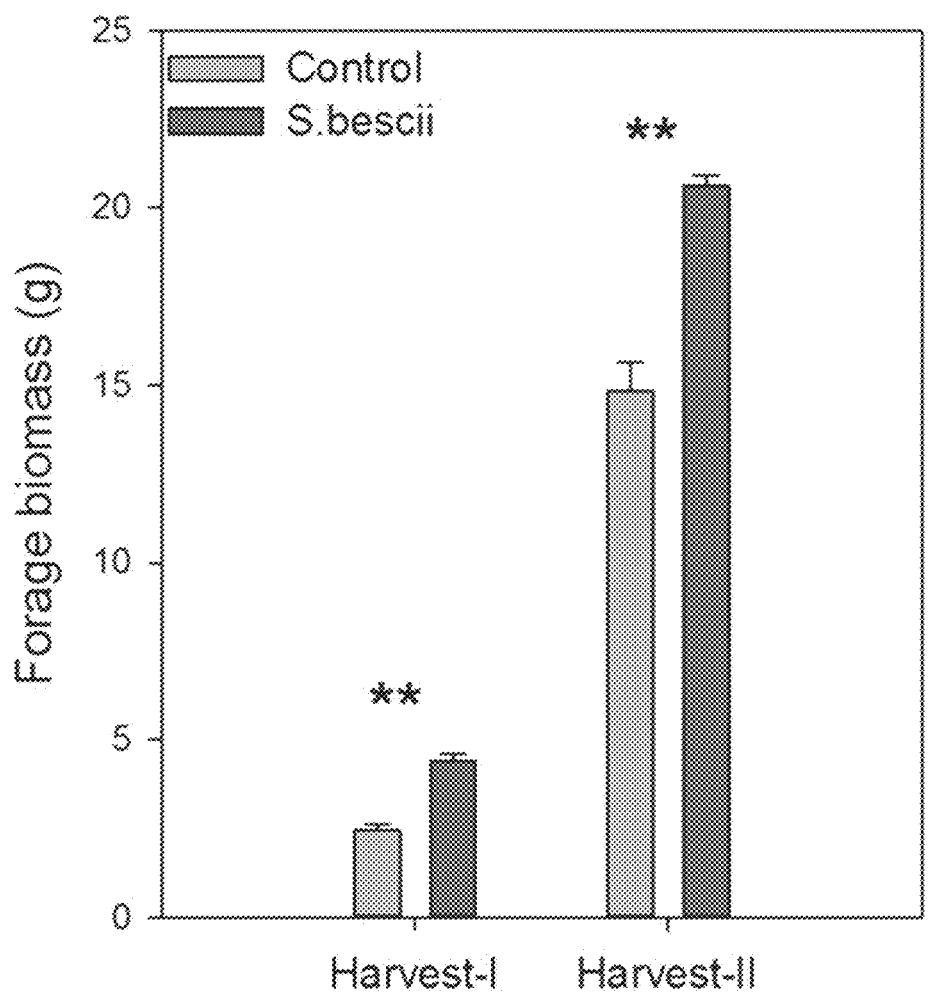
FIG. 17A shows the effect of *S. bescii* colonization on forage biomass in winter wheat under phosphorous-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 17B:
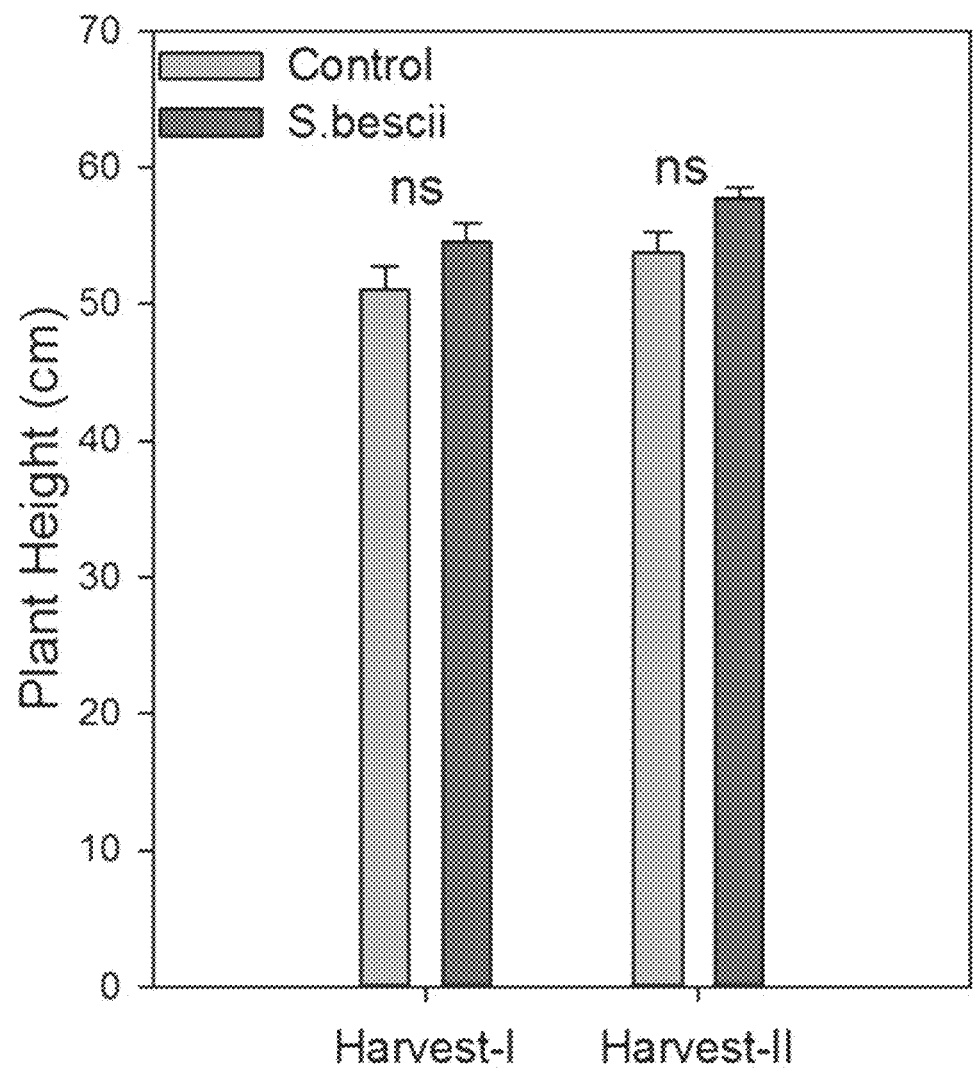
FIG. 17B shows the effect of *S. bescii* colonization on plant height in winter wheat under phosphorous-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 17C:
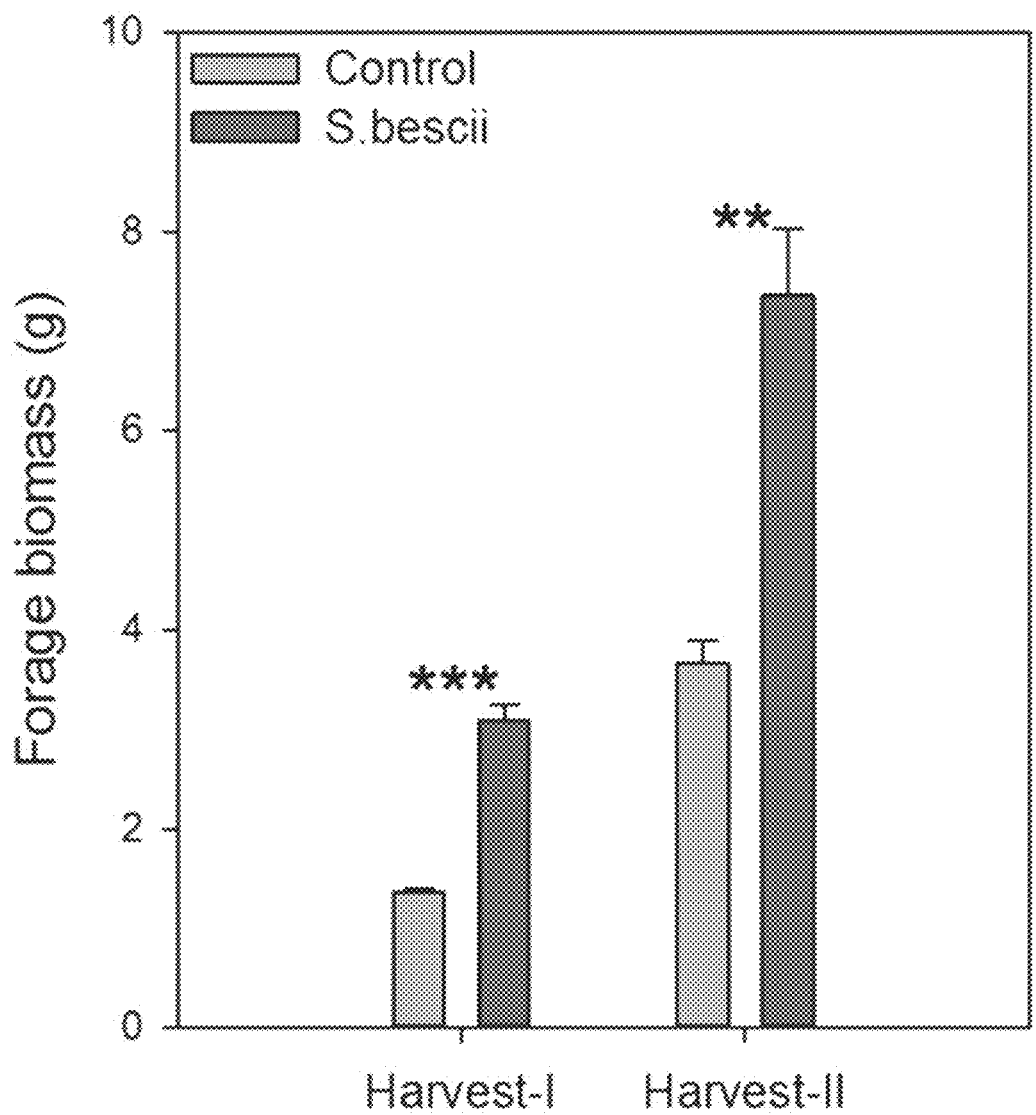
FIG. 17C shows the effect of *S. bescii* colonization on forage biomass in winter wheat under nitrogen-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 17D:
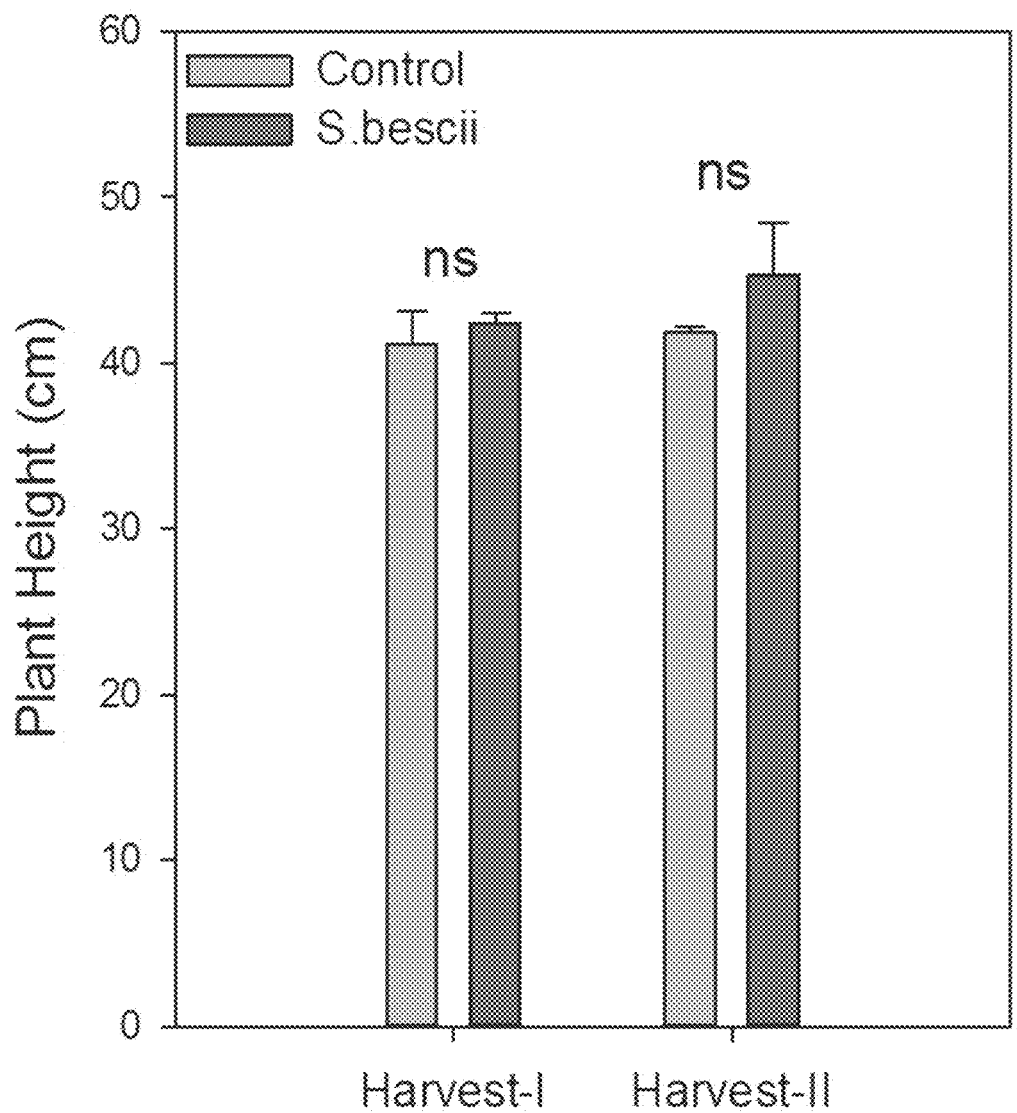
FIG. 17D shows the effect of *S. bescii* colonization on plant height in winter wheat under nitrogen-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).

Effect of *S. bescii* Colonization on Biomass, Forage Biomass and Plant Height Under Phosphorous-Deficient and Nitrogen-Deficient Conditions in Winter Wheat Winter wheat, cultivar NF101 (*Triticum aestivum* L) seedlings were colonized in vitro in minimal (M) media with *S. bescii* following the same protocol as in Example 6. Two different types of M media, namely (a) without phosphorous and (b) without nitrogen were used in this example. After 2 weeks, colonized seedlings and un-inoculated control seedlings were transplanted in 1 gallon pots containing autoclaved Metromix as potting mix. Metromix was washed with clear water to get rid of any available traces of nitrogen and phosphorous. Two identical sets of plants for each treatment were maintained in the greenhouse for estimation of forage biomass four weeks (Harvest-I) and eight weeks (Harvest-II) after transferring into the greenhouse, respectively. Plants grown in M media without nitrogen or phosphorous were watered with ½ strength Hoagland's solution without nitrogen or phosphorous, respectively, to estimate the effect of nitrogen or phosphorous deficiency. The experiment was conducted in three replicates. Un-inoculated plants were maintained in the same way and were used as a control for data analysis. Photographs of five replicate plants for each treatment were taken and are shown in FIGS. 16A-16B. The data were analyzed using ANOVA. When a significant F-test was observed, treatment means were compared using lest significant differences (LSD) at p<0.05 using Costat statistical software 6.4 (Cohort, Berkeley, Calif., United States). The results were plotted graphically using SigmaPlot 12.5 (Systat Software, San Jose, Calif., United States) as shown in FIGS. 17A-17D. As shown, *S. bescii* colonization enhances biomass of winter wheat under both nitrogen-deficient and phosphorous deficient conditions (FIGS. 16A-16B) and significantly enhances forage biomass in winter wheat under both nitrogen-deficient and phosphorous-deficient conditions (FIGS. 17A, 17C) as compared to un-inoculated winter wheat.

Example 8

Effect of *S. bescii* Colonization on Grain Yield in Winter Wheat

Winter wheat, cultivar NF101 (*Triticum aestivum* L) seedlings were colonized in the greenhouse using a bentonite clay-based inoculation protocol. Bentonite clay particles were thoroughly sieved using mesh size 10 (2 mm) to get a uniform particle size. One-liter media bottles were filled with 400 ml of sterile clay particles by volume and subsequently sterilized by autoclave two times with a gap of 2 days. Thereafter, 150 ml of Modified Melin Norkan's broth pH 7 was added to each bottle and sterilized one more time by autoclave before inoculating with the seed culture. Each bottle was inoculated with 50 ml of a 4-week old *S. bescii* liquid culture (Modified Melin Norkan's broth) prepared in 250-ml Erlenmeyer flasks. An equivalent amount of Modified Melin Norkan's broth was added to a control set of bottles. Both the control and the incoualted bottles were incubated in a slanted, stationary position at 24° C. for 8 weeks. The bottles were shaken once per week for uniform distribution of the seed culture. After incubation, the clay particles coated with or without *S. bescii* were air dried overnight at room temperature under a laminar hood chamber.

For inoculation using bentonite clay, a uniform hole of 5 cm depth was made in the center of D25L single cell root trainers (5 cm in diameter by 25 cm in height; Stuewe & Sons, Inc., Oregon, United States) filled with non-sterile Metromix-350 medium (Scotts-Sierra Horticultural Products, Marysville, Ohio, United States) using a 14-ml propylene round bottom tube (BD Falcon, N.J., United States). Clonally propogated seedlings were directly transplanted into this hole. Thereafter, each hole was filled with one half tablespoon of bentonite clay coated with *S. bescii* or the control clay particles lacking the fungus.

Figure 18A:
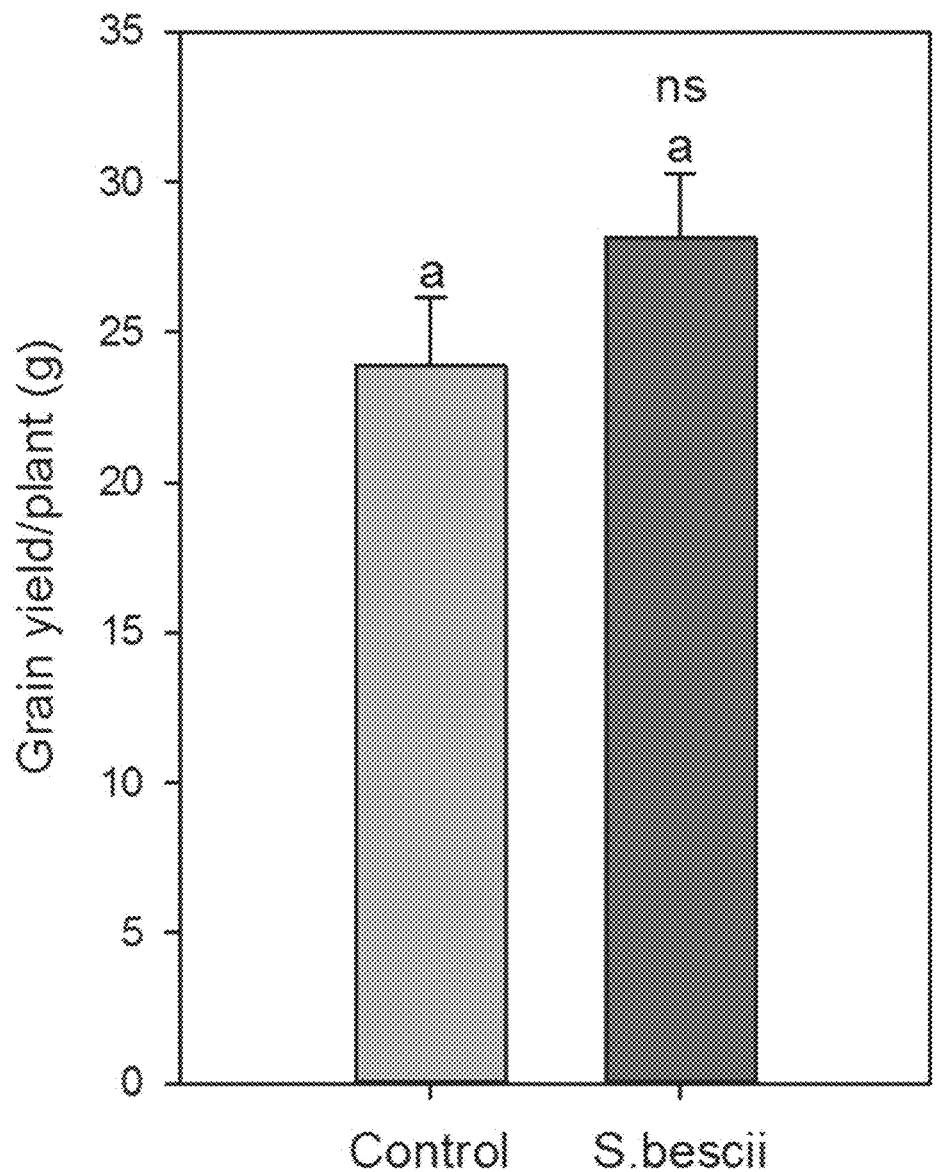
FIG. 18A shows the effect of *S. bescii* colonization on grain yield in grams of winter wheat in field conditions. Error bar denotes standard error of mean. Significant effects are marked as follows: $0.01 \leq p \leq 0.05$ (*); $0.001 \leq p \leq 0.01$ (); $p \leq 0.001$ (*); and $p \leq 0.05$ (ns).
Figure 18B:
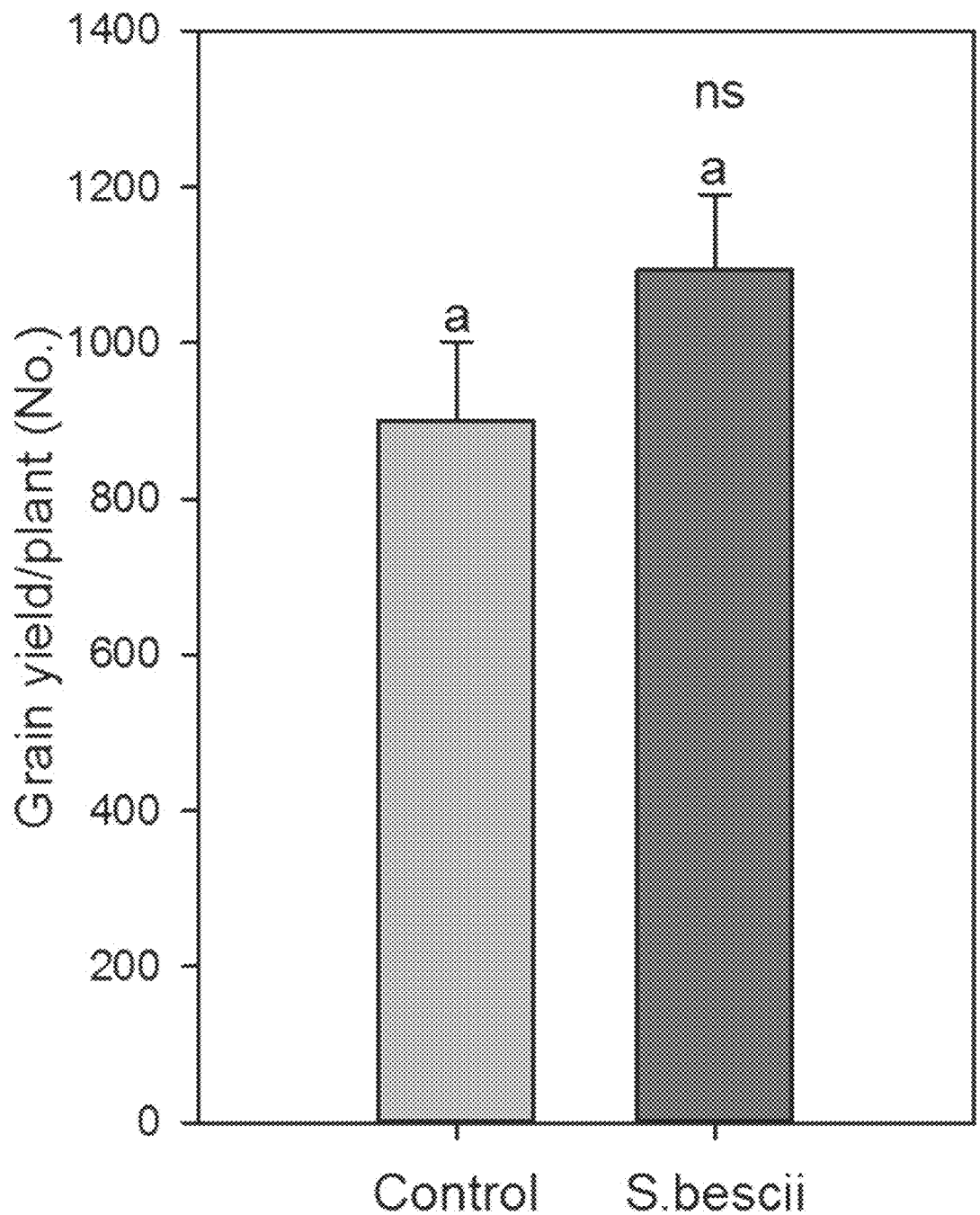
FIG. 18B shows the effect of *S. bescii* colonization on grain yield (number) of winter wheat in field conditions. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).

After 2 weeks, colonized seedlings as well as mock inoculated seedlings were transplanted in the Noble Research Institute's field located in Ardmore, Okla. using a seedling planter. All the treatments were arranged in a randomized complete block design. At the end of the wheat growing season, the crop was harvested for the estimation of grain yield. The experiment was conducted in fifteen replicates. The data were analyzed using ANOVA. When a significant F-test was observed, treatment means were compared using lest significant differences (LSD) at p<0.05 using Costat statistical software 6.4 (Cohort, Berkeley, Calif., United States). The results were plotted graphically using SigmaPlot 12.5 (Systat Software, San Jose, Calif., United States) as shown in FIGS. 18A-18B which show an increase in grain yield with *S. bescii* of approximately 20%.

Example 9

Colonization of Rice by *S. bescii*

Figure 19A:
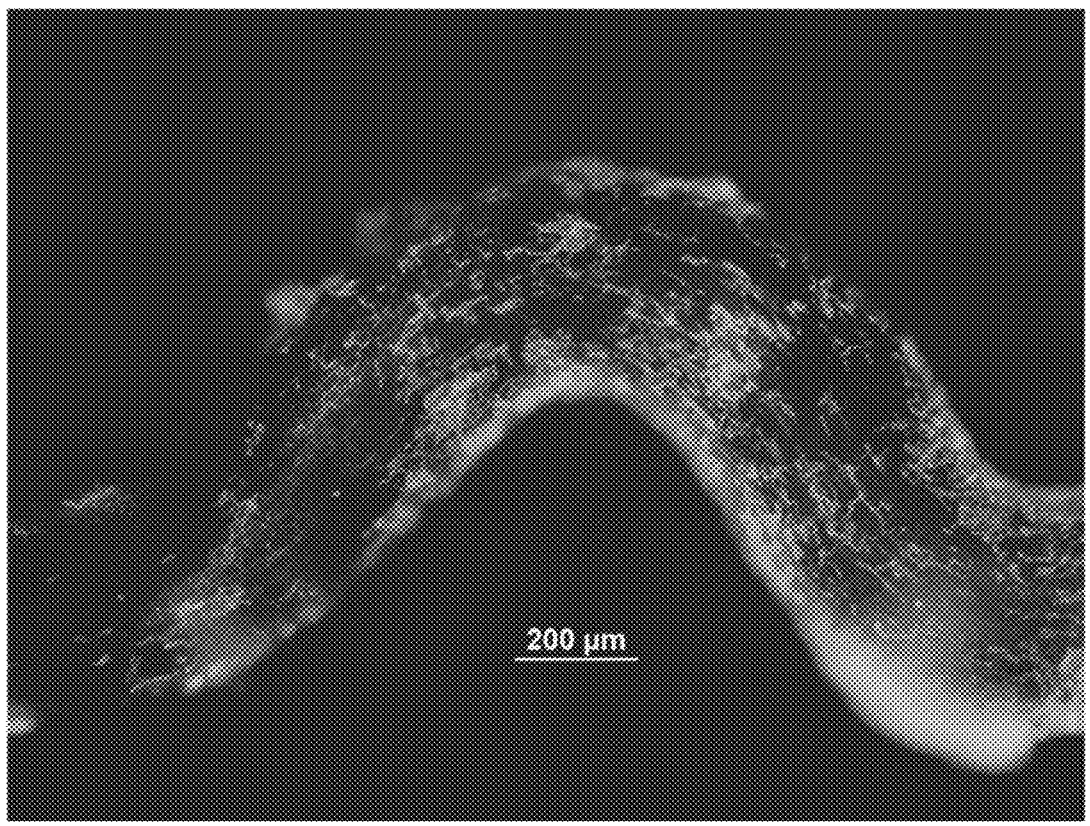
FIG. 19A shows a fluorescence micrograph of colonization of a rice root colonized with *S. bescii*. Scale bar=200 μm.
Figure 19B:
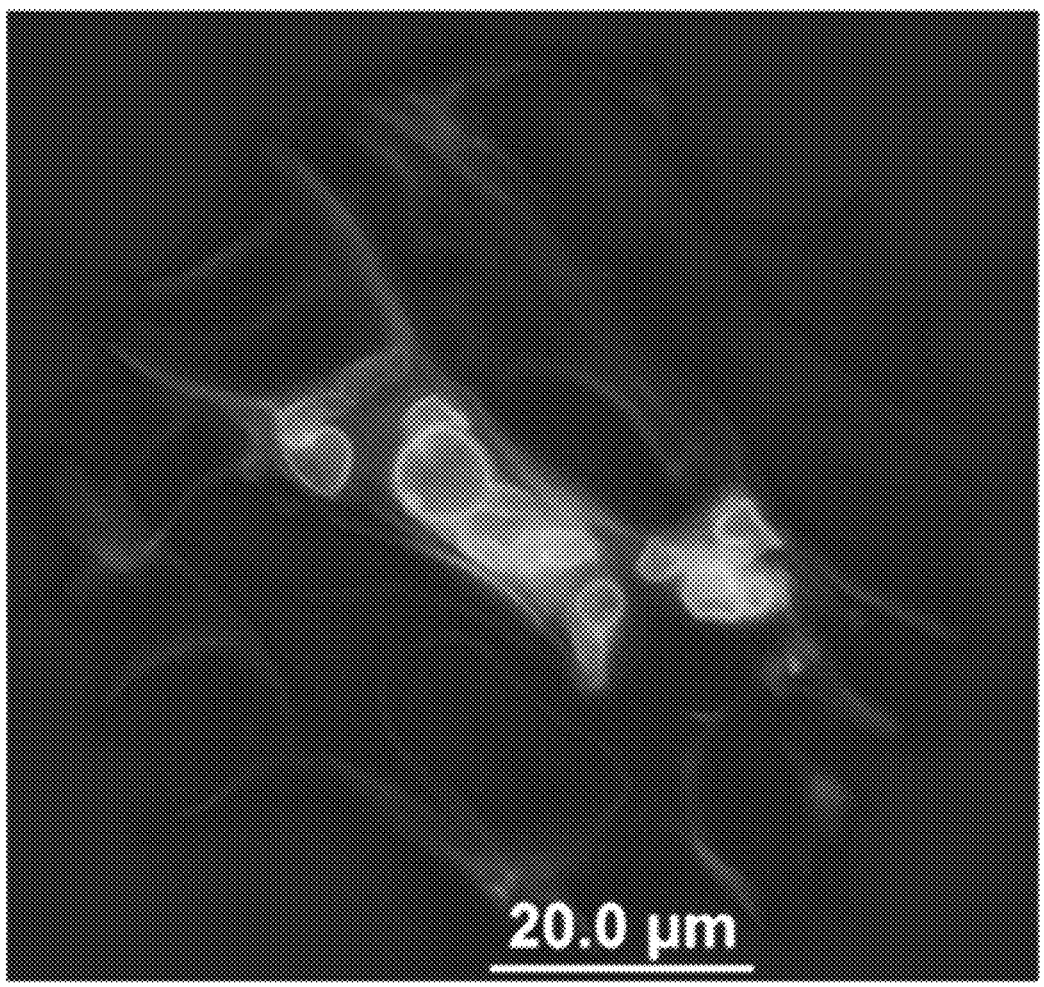
FIG. 19B shows a fluorescence micrograph of a magnified image of a colonized single root cell of rice. Scale bar=20.0 μm.
Figure 19C:
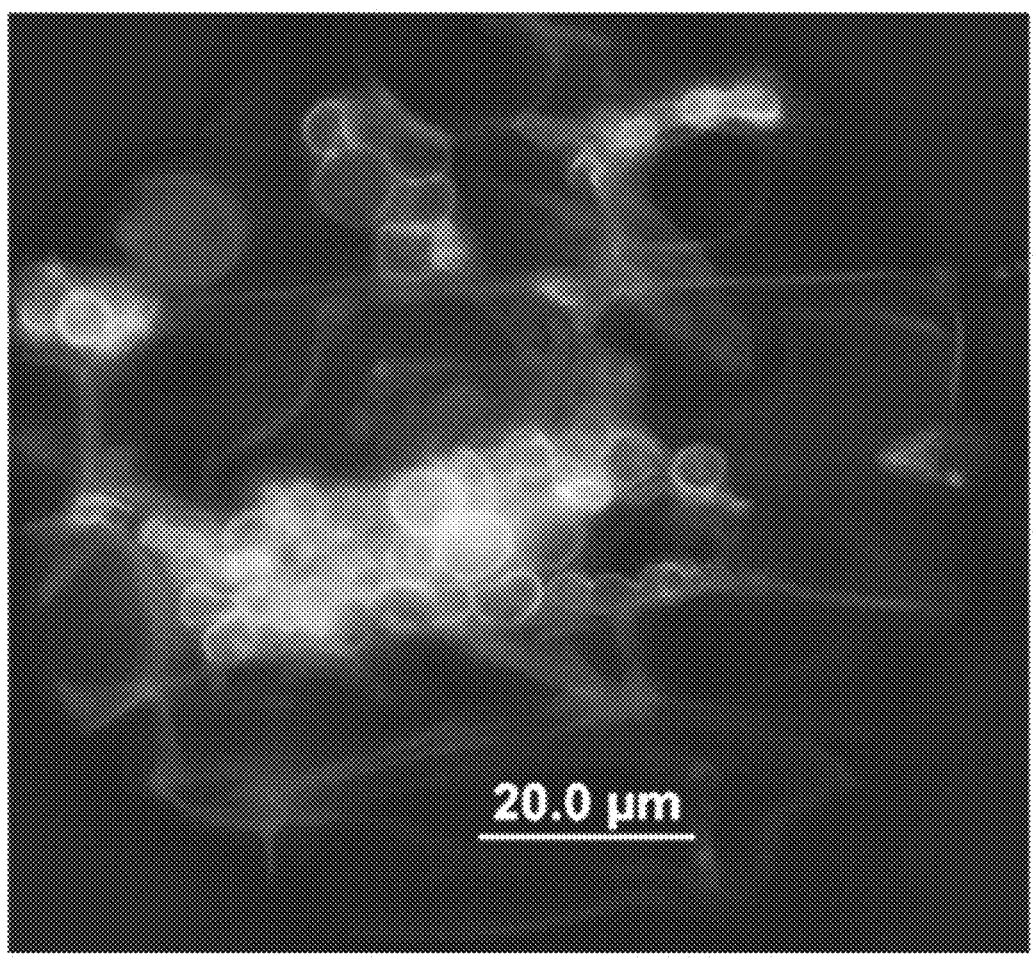
FIG. 19C shows a fluorescence micrograph of a magnified image of a colonized single root cell of rice. Scale bar=20.0 μm.

Rice (*Oryza sativa* L.) seeds were surface sterilized following standard protocol and germinated in vitro in M media. Seedlings were colonized in vitro with *S. bescii*. 2 weeks post colonization, plants were harvested and roots and shoots were segregated. Roots were immediately fixed in 50% ethanol. Fixed roots were cut into 1 cm long pieces and stained with WGA-AF® dye (green) for visualization of fungus and counter stained with propidium iodide (red) for visualization of root cells by fluorescence microscopy. An image of a rice root fragment colonized by *S. bescii* and magnified images of colonized single root cells are shown in FIGS. 19A and 19B-19C, respectively. These results demonstrate colonization of rice roots with *S. bescii*.

Example 10

Colonization of Cotton by *S. bescii*

Figure 20A:
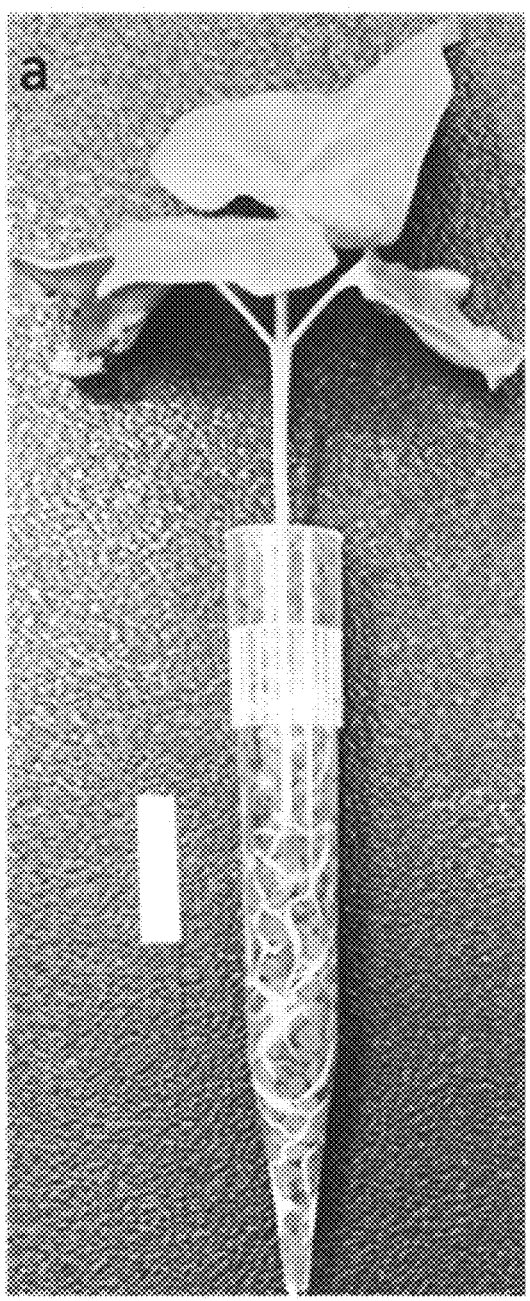
FIG. 20A shows a photograph of a cotton seedling colonized with *S. bescii*.
Figure 20B:
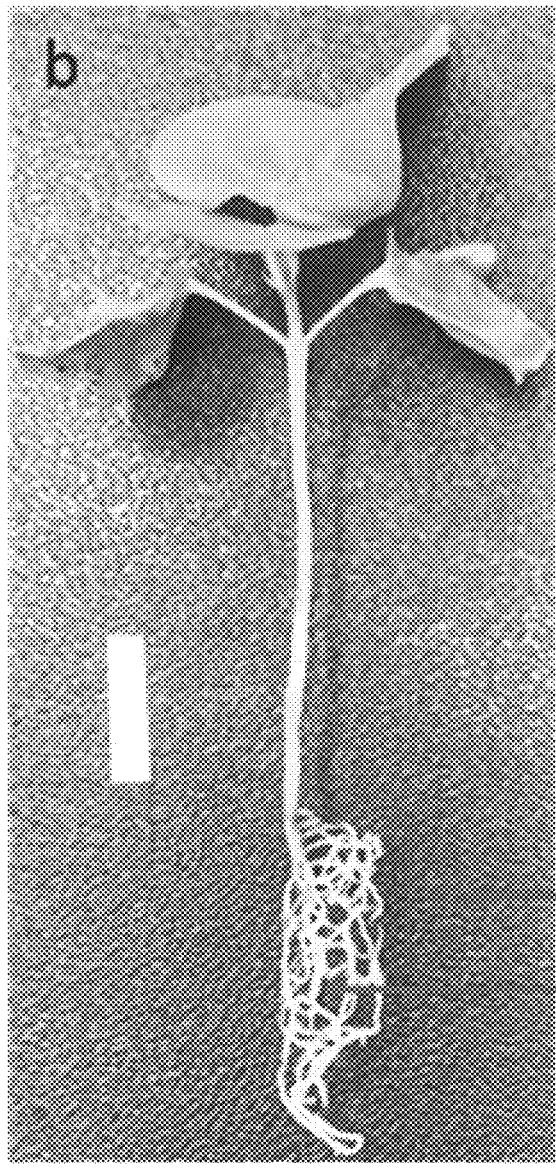
FIG. 20B shows a photograph of a cotton seedling colonized with *S. bescii* showing lateral and primary roots.
Figure 20C:
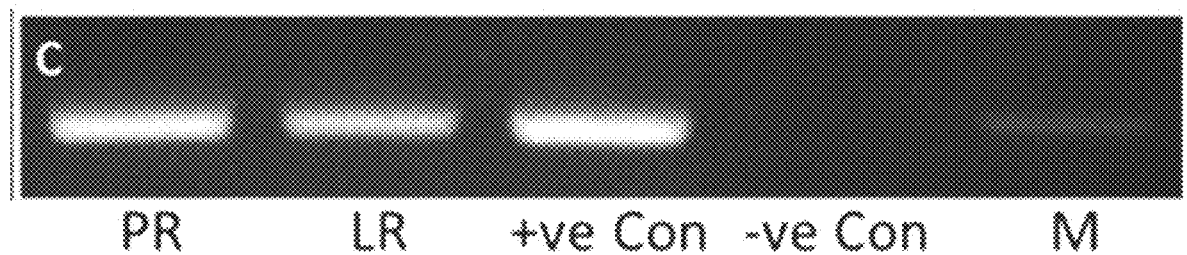
FIG. 20C shows an agarose gel electrophoresis of an amplicons from PCR of primary root (PR), lateral root (LR), positive control (+ve Con), negative control (-ve Con) using *S. bescii* specific primers and a molecular weight marker (M).
Figure 20D:
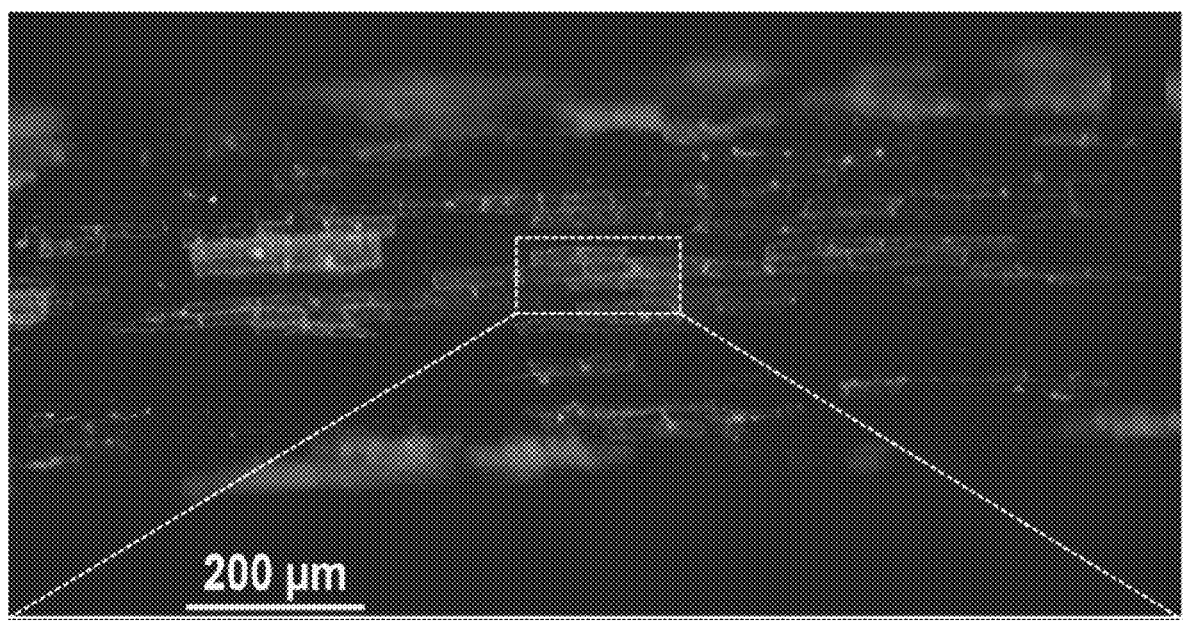
FIG. 20D shows a fluorescence micrograph of a cotton root colonized with *S. bescii*. Scale bar=200 μm.
Figure 20E:
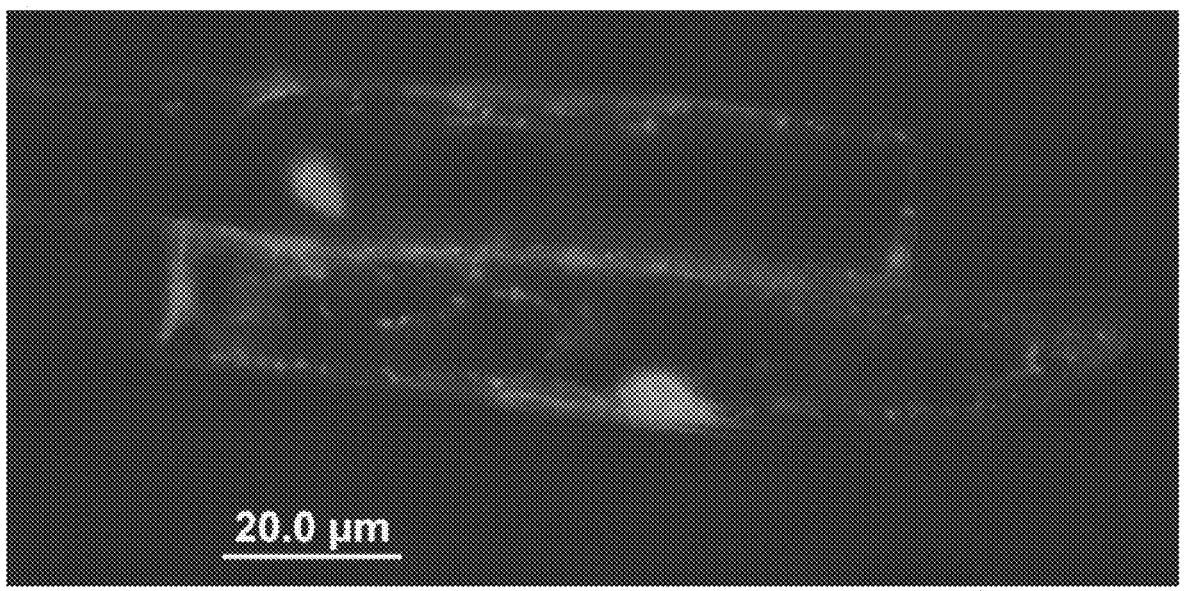
FIG. 20E shows a fluorescence micrograph of a cotton root colonized with *S. bescii*. Scale bar=20.0 μm.

Cotton (*Gossypium hirsutum* L.) seeds were surface sterilized following standard protocol and germinated in moist sterile filter paper. Seedlings were colonized using the bentonite clay-based method of Example 8. 2 weeks post-colonization, plants were harvested and primary root (PR) and lateral roots (LR) were segregated as shown in FIGS. 20A-20B and PCR done using *S. bescii* primers (SEQ ID NO: 11 and SEQ ID NO: 12). A positive PCR result indicates successful colonization as shown in FIG. 20C. Colonized root samples were also microscopically observed for more direct evidence of colonization. Colonized roots were fixed in 50% ethanol, then cut into 1 cm long pieces and stained with WGA-AF® dye (green) for visualization of fungus and counterstained with propidium iodide (red) for visualization of root cells by fluorescence microscopy as shown in FIGS. 20D-20E. The results demonstrate successful colonization of cotton by both PCR and microscopy.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated.

What is claimed is:

1. A composition comprising a carrier material coated or impregnated with a *Serendipita vermifera* ssp. *bescii* endophyte, wherein the *Serendipita vermifera* ssp. *bescii* endophyte comprises a nucleotide sequence of SEQ ID NO: 2, and wherein the carrier material is bentonite clay.

2. The composition of claim 1, wherein the *Serendipita vermifera* ssp. *bescii* endophyte comprises a nucleotide sequence of SEQ ID NO: 1.

3. A method comprising,
inoculating a host plant with an inoculum by contacting the host plant with the inoculum comprising a carrier material coated or impregnated with a *Serendipita vermifera* ssp. *bescii* endophyte comprising the nucleotide sequence of SEQ ID NO: 2 under conditions sufficient to promote colonization of the roots of the host plant by the *Serendipita vermifera* ssp. *bescii* endophyte, wherein the carrier material is bentonite clay.

4. The method of claim 3, wherein the inoculating is performed by adding the inoculum to the living soil in contact with the roots of the host plant.

5. The method of claim 3, wherein the host plant is a monocot or a dicot.

6. The method of claim 3, wherein the host plant is chosen from wheat, durum wheat, tall wheatgrass, western wheatgrass, maize, rice, sorghum, onion, asparagus, millet, meadow fescue, tall fescue, cereal rye, Russian wild rye, oats, bermudagrass, Kentucky bluegrass, big bluestem, little bluestem, blue grama, black grama, side-oat, grama, johnsongrass, bufallograss, creeping bentgrass, alfalfa, rose, tomato, blueberry, cotton, pepper, common bean, lentil, peas, eggplant, watermelon, coffee, apples, plums, sweet cherry, squash, broccoli, turnips, fernaiums, strawberry, soybean and pecan.

7. The method of claim 3, wherein the *Serendipita vermifera* ssp. *bescii* endophyte comprises the nucleotide sequence of SEQ ID NO: 1.

8. A synthetic combination of a carrier material coated or impregnated with a *Serendipita vermifera* ssp. *bescii* endophyte and a host plant, wherein the *Serendipita vermifera* ssp. *bescii* endophyte comprises the nucleotide sequence of SEQ ID NO: 2, and wherein the carrier material is bentonite clay.

9. The synthetic combination of claim 8, wherein the host plant is a seed.

10. A method for colonizing a host plant with a *Serendipita vermifera* ssp. *bescii* endophyte, comprising:
placing bentonite clay particles coated or impregnated with a *Serendipita vermifera* ssp. *bescii* endophyte comprising the nucleotide sequence of SEQ ID NO: 2 in living soil;
planting a seed of the host plant in contact with the bentonite clay particles under conditions sufficient for the *Serendipita vermifera* ssp. *bescii* endophyte to colonize the roots of the host plant.

* * * * *